(12) United States Patent  
Fantini

(10) Patent No.: US 7,962,187 B2  
(45) Date of Patent: Jun. 14, 2011

(54) OPTICAL IMAGING AND OXIMETRY OF TISSUE

(75) Inventor: Sergio Fantini, Winchester, MA (US)

(73) Assignee: Tufts University, Medford, MA (US)

(*) Notice: Subject to any disclaimer, the term of this patent is extended or adjusted under 35 U.S.C. 154(b) by 2115 days.

(21) Appl. No.: 10/507,336

(22) PCT Filed: Mar. 13, 2003

(86) PCT No.: PCT/US03/07766
§ 371 (c)(1),
(2), (4) Date: Jun. 28, 2005

(87) PCT Pub. No.: WO03/077750
PCT Pub. Date: Sep. 25, 2003

(65) Prior Publication Data
US 2006/0106293 A1      May 18, 2006

Related U.S. Application Data

(60) Provisional application No. 60/364,239, filed on Mar. 13, 2002.

(51) Int. Cl.
*A61B 5/00*        (2006.01)
(52) U.S. Cl. ......... 600/310; 600/473; 600/475; 600/323
(58) Field of Classification Search .............. 606/40–49, 606/36, 38, 710.12, 15–18; 600/424, 160, 600/310, 407, 473–476, 323; 356/432, 436; 372/28; 382/128, 131
See application file for complete search history.

(56) References Cited

U.S. PATENT DOCUMENTS

| | | | | |
|---|---|---|---|---|
| 4,515,165 | A * | 5/1985 | Carroll | 600/475 |
| 5,079,698 | A * | 1/1992 | Grenier et al. | 382/128 |
| 5,285,783 | A | 2/1994 | Secker | |
| 5,830,141 | A * | 11/1998 | Makram-Ebeid et al. | 600/407 |
| 5,999,836 | A * | 12/1999 | Nelson et al. | 600/407 |
| 6,002,958 | A * | 12/1999 | Godik | 600/407 |
| 6,064,474 | A * | 5/2000 | Lee et al. | 356/39 |
| 6,192,260 | B1 * | 2/2001 | Chance | 600/310 |
| 6,216,021 | B1 * | 4/2001 | Franceschini et al. | 600/310 |
| 6,226,540 | B1 | 5/2001 | Bernreuter | |

(Continued)

OTHER PUBLICATIONS

Fantini, S. et al., "Assessment of the Size, Position, and Optical Properties of Breast Tumors in Vivo by Non-Invasive Optical Methods", Applied Optics 37, 1982-1989, 1998.*

(Continued)

*Primary Examiner* — Francis Jaworski
(74) *Attorney, Agent, or Firm* — Fish & Richardson P.C.

(57) ABSTRACT

Systems and methods are disclosed for detecting at least one region of a sample having an absorption level different from a background level of absorption in the sample by obtaining thicknesses of the sample and intensities of light transmitted through the sample at a plurality of locations. The system includes glass plates (10) for compressing the tissue, distance sensors (20, 30), illuminations fibers (40) connected to a light source (70), and collection fibers (50) connected to spectrograph (110). Spatial second derivatives are calculated from products of the thicknesses of the sample and the intensities of the transmitted light for the locations. The data points are compared to detect the region of the sample having an absorption level different from the background level of absorption within the sample. The new systems and method can be used to optically image, detect, and characterize tissue, lesions, such as cancer.

15 Claims, 20 Drawing Sheets

U.S. PATENT DOCUMENTS

| | | | | |
|---|---|---|---|---|
| 6,230,045 | B1* | 5/2001 | Hoogenraad et al. | 600/473 |
| 6,587,703 | B2* | 7/2003 | Cheng et al. | 600/310 |
| 6,594,513 | B1* | 7/2003 | Jobsis et al. | 600/328 |
| 6,665,557 | B1* | 12/2003 | Alfano et al. | 600/473 |
| 6,985,763 | B2* | 1/2006 | Boas et al. | 600/323 |
| 7,006,676 | B1* | 2/2006 | Zeylikovich et al. | 382/131 |
| 7,142,304 | B1* | 11/2006 | Barbour et al. | 356/432 |
| 2003/0225337 | A1* | 12/2003 | Scharf et al. | 600/508 |
| 2006/0173352 | A1* | 8/2006 | Lilge et al. | 600/476 |
| 2007/0219450 | A1* | 9/2007 | Azar et al. | 600/476 |

OTHER PUBLICATIONS

Cerussi, A.E. et al., "Spectroscopy enhances the information content of optical mammography", *Journal of Biomedical Optics* 7, pp. 60-71, 2002.

Dehghani, H. et al., "Multiwavelength three-dimensional near-infrared tomography of the breast: initial simulation, phantom, and clinical results", *Applied Optics* 42, pp. 135-145, 2003.

Fantini, S. et al., "Frequency-domain optical mammography: Edge effect corrections", *Medical Physics* 23, pp. 149-157, 1996.

Fantini, S. et al., "Assessment of the Size, Position, and Optical Properties of Breast Tumors in Vivo by Non-Invasive Optical Methods", *Applied Optics* 37, pp. 1982-1989, 1998.

Franceschini, M.A. et al., "Frequency-Domain Techniques Enhance Optical Mammography: Initial Clinical Results", *Proceedings of the National Academy of Science of the USA* 94, pp. 6468-6473, 1997.

Grosenick, D. et al., "Concentration and oxygen saturation of haemoglobin of 50 breast tumors determined by time-domain optical mammography", *Physics in Medicine and Biology* 49, pp. 1165-1181, 2004.

Hanson, K.M., presentation entitled "Optical tomography: seeing inside the body", available from http://public.lanl.gov/kmh/talks/graz99.pdf, Apr. 26, 1999.

Heffer, E.L. and Fantini, S., "Quantitative oximetry of breast tumors: A novel, near-infrared method that identifies two optimal wavelengths for each tumor", *Applied Optics* 41, pp. 3827-3839, 2002.

Heffer, E.L. et al., "Near-infrared imaging of the human breast: Complementing hemoglobin concentration maps with oxygenation images", *Journal of Biomedical Optics* 9, pp. 1152-1160, 2004.

Hohenberger, P. et al., "Tumor oxygenation correlates with molecular growth determinants in breast cancer", *Breast Cancer Research and Treatment* 48, pp. 97-106, 1998.

Hoogenraad, J.H., "First Results from the Philips Optical Mammoscope", *Photon Propagation in Tissues III* (D. Benaron, B. Chance, and M. Ferrari, eds.), *Proceedings of the SPIE* 3194, pp. 184-190, 1998.

Kaschke, M. et al., "Transillumination Imaging of Tissue by Phase Modulation Techniques", *Advances in Optical Imaging and Photon Migration* (R.R. Alfano, ed.), *Proceedings of the Optical Society of America* 21, pp. 88-92, 1994.

Peters, V.G. et al., "Optical Properties of Normal and Diseased Human Breast Tissues in the Visible and Near-Infrared", *Physics in Medicine and Biology* 35, pp. 1317-1334, 1990.

Vaupel, P., Kallinowski, F. and Okunieff, P., "Blood Flow, Oxygen and Nutrient Supply, and Metabolic Microenvironment of Human Tumors: A Review", *Cancer Research* 49, pp. 6449-6465, 1989.

Yamashita, Y. and Kaneko, M., "Visible and Infrared Diaphanoscopy for Medical Diagnosis," in *Medical Optical Tomography: Functional Imaging and Monitoring*, vol. IS11 of *SPIE Institutes for Advanced Optical Technologies* (G.J. Muller et al., eds.), SPIE Optical Engineering Press: Bellingham, Washington, 1993, pp. 283-316.

* cited by examiner

| λ (nm) | Silicone Mixture A | | Silicone Mixture B | | Liposyn suspension | |
|---|---|---|---|---|---|---|
| | $\mu_a$ (cm$^{-1}$) | $\mu_s'$ (cm$^{-1}$) | $\mu_a$ (cm$^{-1}$) | $\mu_s'$ (cm$^{-1}$) | $\mu_a$ (cm$^{-1}$) | $\mu_s'$ (cm$^{-1}$) |
| 752 | 0.062(3) | 9.8(4) | 0.148(6) | 9.3(4) | 0.029(1) | 12.2(6) |
| 778 | 0.055(2) | 9.7(4) | 0.127(5) | 9.8(4) | 0.028(1) | 11.7(6) |
| 786 | 0.058(2) | 9.8(4) | 0.130(5) | 9.8(4) | 0.026(1) | 11.6(6) |
| 813 | 0.055(2) | 9.3(4) | 0.119(5) | 9.6(4) | 0.024(1) | 11.1(5) |
| 830 | 0.054(2) | 9.4(4) | 0.117(5) | 9.6(4) | 0.031(2) | 10.5(5) |
| 840 | 0.053(2) | 8.9(4) | 0.111(5) | 9.4(4) | 0.039(2) | 10.2(5) |

N" at 690 nm

Oxygenation Index

N at 690 nm
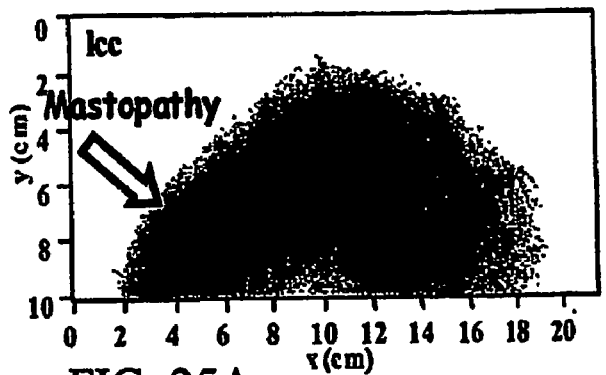
FIG. 25A
N" at 690 nm
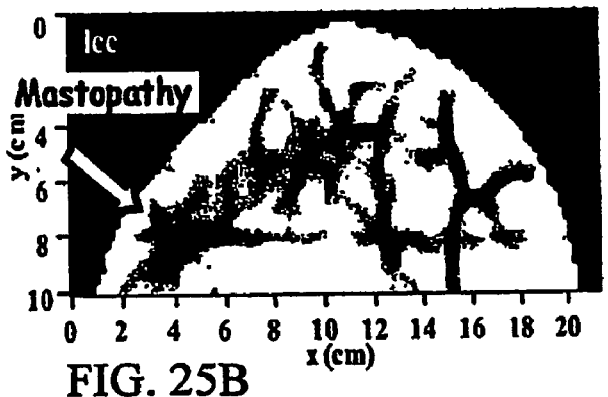
FIG. 25B
Oxygenation Index
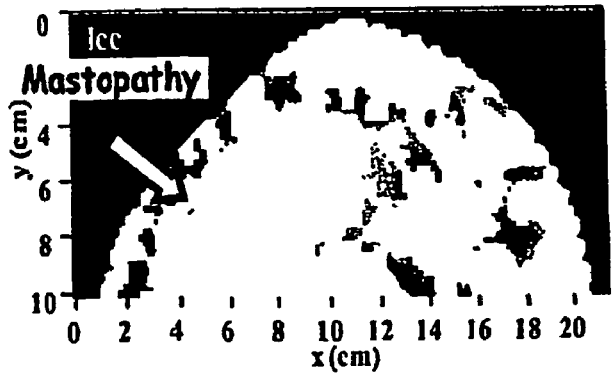

OPTICAL IMAGING AND OXIMETRY OF TISSUE

CLAIM OF PRIORITY

This application claims priority under 35 USC §119(e) to U.S. Provisional Patent Application Ser. No. 60/364,239, filed on Mar. 13, 2002, the entire contents of which is hereby incorporated by reference in its entirety.

TECHNICAL HELD

This invention relates to optical methods, and more particularly to optical methods of imaging and oximetry.

BACKGROUND

Optical techniques provide a safe and non-invasive means of studying human tissue. For example, optical mammography is a technique for detecting cancer in the human breast. This technique uses wavelengths of light in the near infrared (NIR) spectrum to provide an image where contrast is based on the absorption of the light by hemoglobin. Hemodynamic changes such as an increase in the vascular density (resulting from angiogenesis) and changes in the blood flow and oxygenation typically occur at tumor sites. See, e.g., S. Zhou et al., Proc. SPIE 2979:98-106, 1997. The increase in vascular density induces a local increase in the optical absorption that may allow for the detection of breast lesions, which can be benign or malignant.

The oxygenation level of a lesion has been said to indicate whether a lesion is benign or malignant. Measurements of the partial pressure of oxygen in tumors have shown that hypoxic or anoxic conditions often exist in malignant tumors, but not in benign lesions. Se P. Vaupel et al., Cancer Res. 51, 3316-3322, 1991; P. Hohenberger et al., Breast Cancer Research and Treatment 48, 97-106, 1998; and P. Vaupel et al., Seminars in Oncology 2, 29-35, 2001. Therefore, measurements of the oxygenation levels of tissues in vivo can distinguish benign from malignant lesions in the human breast.

SUMMARY

The invention features improved systems and techniques for imaging a region of tissue using optical methods and improved techniques for measuring the oxygenation level of regions of interest in tissue in a living subject. These techniques are non-invasive, using safe levels of optical radiation. The optical imaging systems and techniques can be applied to a wide variety of samples, including human brain, breast, and muscle tissue, as well as any organ that is optically accessible. These techniques provide enhanced image contrast, facilitating detection of lesions and tumors and differentiating between benign and malignant varieties. In addition, the new techniques for measuring the oxygenation level of a region of interest, such as a lesion or tumor, are useful, e.g., to further assess the malignancy of these regions.

In general, the new systems and techniques improve the diagnostic capability of optical mammography. While these systems and methods can be used to image breast tissue and oximetry of breast tumors, they can also be used to measure the oxygenation level of other hemoglobin-rich localized tissue areas. For example, the focal increase in cerebral hemoglobin concentration induced by selected cerebral activity, a localized hematoma, and large blood vessels can be investigated using the methods presented here to measure oxygenation levels.

In one aspect, the invention features imaging systems including one or more light sources that provide light to a sample, a detector that detects light transmitted through the sample, and a processor that calculates data using spatial second derivatives of products of thicknesses of the sample and intensities of the transmitted light. The new systems can include a number of features. For example, the light sources can be laser diodes, the detectors can be photomultiplier tubes or avalanche photodiodes, and the processor can be a computer. The systems can be implemented using known equipment, and the light sources and detectors can be separated by a fixed distance, e.g., to simplify data analysis. In addition, the systems can include a monitor to display an image of the data and/or a computer-readable medium to store the data.

The invention also features a computer-readable medium having a program that is used by a processor to receive data from a sample that represents measures of thicknesses of the sample and intensities of light transmitted through the sample, and to process the data from the sample using spatial second derivatives of products of the thicknesses of the sample and intensities of the transmitted light to generate values that represent an image of the sample. This computer-readable medium is useful to transport and distribute the new algorithms to various users.

In a further aspect, the invention features a computer-readable medium including a program that is used by a processor to receive data from a sample that represent measures of intensities of light transmitted through the sample for at least two wavelengths of light, select a pair of wavelengths to minimize a difference between relative changes in the intensities of the light transmitted through a region of the sample, where the relative changes in intensities of the light are measured relative to a background intensity of light transmitted through the sample, and process the relative changes in intensities of the light at the pair of wavelengths using measures of a background reduced scattering coefficient of the sample at the pair of wavelengths and molar extinction coefficients for deoxy-hemoglobin and oxy-hemoglobin to generate values that represent an absolute level of oxygenation of the region of the sample.

The computer-readable medium can also include both programs to process spatial second derivatives and to calculate absolute levels of oxygenation of a sample, as described herein.

In other aspects, the invention features methods that can be carried out using the new systems, such as methods of detecting at least one region of a sample having an absorption level different from a background level of absorption in the sample. These methods involve obtaining thicknesses of the sample and intensities of light transmitted through the sample at a plurality of locations, calculating data points for the locations using spatial second derivatives of products of the thicknesses of the sample and the intensities of the transmitted light, and comparing the data points to detect a region of the sample having an absorption level different from a background level of absorption within the sample.

Using the spatial second derivatives enhances differentiation of regions of the sample having different levels of absorption from the background level of absorption within the sample. In addition, this approach has the advantages of being insensitive to the size, shape, and depth of the region within the sample. Embodiments of this aspect of the invention include one or more of the following features. The sample can be tissue, e.g., breast, brain, or muscle tissue. Consequently, the methods and systems are useful in performing optical mammography, studying brain activation, and identifying ischemic or underperfused regions in muscle. The region of the sample having an absorption level different from the background level of absorption within the sample can be a lesion or tumor. This region can be cancerous. Thus, the systems and methods can be applied to identify lesions, including cancerous tumors, within breast tissue. The systems and methods can also be used to identify tumors regardless of their size, shape, or depth of the tumor within the breast.

The methods can further involve illuminating the sample with light and detecting light transmitted through the sample. This light can have two or more wavelengths. Illumination with multiple wavelengths of light is useful to apply the new methods of oximetry discussed herein. One or more of these wavelengths can be in the near infrared region of the spectrum. Infrared light exhibits a desirable amount of absorption within human tissue, e.g., breast tissue. The transmitted light can be generated by coplanar sources and the plurality of locations where the light is detected can be coplanar. Using coplanar sources and detectors facilitates data analysis.

In these systems and methods, the data points $N''(x,y)$ are calculated using the second derivative of an equation $N(x,y)=r_0 ac_0/r(x,y)ac(x,y)$, where x and y are respective x- and y-coordinates of the coplanar locations, $r_0$ is the maximum thickness of the sample, $ac_0$ is the intensity at the location where the thickness of the sample is $r_0$, $r(x,y)$ is the thickness of the sample at location $(x,y)$, and $ac(x,y)$ is the intensity at location $(x,y)$. These data points can be displayed in an image, as this formula provides useful data points for imaging. Alternatively or additionally, they can be stored in a computer-readable medium. By storing these data points on a computer-readable medium, the image can be used for later comparison or displayed at alternate locations and times.

In another aspect of the invention, method are used, in the new systems, to calculate an absolute oxygenation level of a region of a sample by selecting a pair of wavelengths of light to minimize a difference between relative changes in intensity of the light transmitted through the region of the sample, where the relative changes in intensity of the light are measured relative to a background intensity of light transmitted through the sample; obtaining measures of background reduced scattering coefficients of the sample at the pair of wavelengths; and calculating the absolute oxygenation level of the region of the sample using the relative changes in intensity of the light at the pair of wavelengths, the measures of the background reduced scattering coefficients of the sample at the pair of wavelengths, and molar extinction coefficients for deoxy-hemoglobin and oxy-hemoglobin.

These methods provide accurate quantitative measurements of the oxygenation level of regions of interest within a sample. Such measurements are valuable to differentiate between benign and cancerous tumors within breast tissue. Using an appropriate pair of wavelengths of light provides measurements that are largely independent of the tumor size, shape, and location inside the breast. It is significant that the pair of wavelengths for the near-infrared measurement of tumor oxygenation is not fixed, but instead depends generally on tumor oxygenation.

These methods (and the computer readable medium) can include the use of the formula $$SO_2 = \frac{\varepsilon_{Hb}(\lambda_2) - \varepsilon_{Hb}(\lambda_1)\frac{\mu'_{so}(\lambda_1)}{\mu'_{so}(\lambda_2)}\frac{\Delta I/I_0|_{max}^{(\lambda_2)}}{\Delta I/I|_{max}^{(\lambda_1)}}}{[\varepsilon_{Hb}(\lambda_2) - \varepsilon_{HbO2}(\lambda_2)] + [\varepsilon_{HbO2}(\lambda_1) - \varepsilon_{Hb}(\lambda_1)]\frac{\mu'_{so}(\lambda_1)}{\mu'_{so}(\lambda_2)}\frac{\Delta I/I_0|_{max}^{(\lambda_2)}}{\Delta I/I|_{max}^{(\lambda_1)}}},$$

where $SO_2$ is the oxygenation level of the region, $\Delta I/I_0|_{max}^{(\lambda_1)}$ is a maximum value of the relative change in intensity at a first wavelength in the pair of wavelengths, $\Delta I/I_0|_{max}^{(\lambda_2)}$ is a maximum value of the relative change in intensity at a second wavelength in the pair of wavelengths;

$$\frac{\mu'_{so}(\lambda_1)}{\mu'_{so}(\lambda_2)}$$

is a ratio of the background reduced scattering coefficient at the first wavelength to the background reduced scattering coefficient at the second wavelength, $\varepsilon_{Hb}(\lambda_1)$ and $\varepsilon_{Hb}(\lambda_2)$ are the molar extinction coefficients for deoxy-hemoglobin at the first and second wavelengths, and $\varepsilon_{HbO2}(\lambda_1)$ and $\varepsilon_{HbO2}(\lambda_2)$ are the molar extinction coefficients for oxy-hemoglobin at the first and second wavelengths. This formula provides accurate values of oxygenation levels and is useful for ascertaining the malignancy of tumors. The difference between the relative changes in intensity can be zero, as this provides an optimal pair of wavelengths.

These methods can also include a number of additional features. For example, the sample can be illuminated with two or more wavelengths of light and the light transmitted through the sample can be detected. The method can also include displaying the absolute oxygenation level of the region in an image and/or storing the absolute oxygenation level of the region in a computer-readable medium. Storage of oxygenation level information facilitates transport and sharing of this information, as well as permitting analysis at another location and/or time.

In another aspect, methods are used to determine whether a tumor in a tissue sample is a malignant tumor or a benign tumor. Thicknesses of the sample and intensities of light transmitted through the sample at a plurality of locations for two wavelengths of light are obtained. Spatial second derivatives of products of the sample thicknesses and the intensities of the transmitted light at the locations for the two wavelengths of light are calculated. An oxygenation level of the tumor is then calculated based on the spatial second derivatives for the two wavelengths of light, the molar extinction coefficients of oxy-hemoglobin for the two wavelengths of light, the molar extinction coefficients of hemoglobin for the two wavelengths of light, relative changes in intensity of the light for the two wavelengths and the measures of the background reduced scattering coefficients of the sample for the two wavelengths. The oxygenation level of the tumor is compared with the oxygenation level of non-tumor regions of the sample to determine whether the tumor is malignant or benign.

These methods provide accurate measurements of the relative oxygenation level of regions of interest within a sample. Such measurements are valuable to differentiate between benign and cancerous tumors within, for example, breast tissue, brain tissue, and muscle tissue.

These methods may use the following formula for calculating an oxygenation level:

$$OL = \frac{\Delta[HbO_2]^*}{\Delta[HbO_2]^* + \Delta[Hb]^*}, \text{ where}$$

$$\Delta[HbO_2]^* = \frac{\left(\sum_i N''(\lambda_i)\varepsilon_{HbO2}(\lambda_i)\right)\left(\sum_i \varepsilon_{Hb}^2(\lambda_i)\right) - \left(\sum_i N''(\lambda_i)\varepsilon_{Hb}(\lambda_i)\right)\left(\sum_i \varepsilon_{HbO2}(\lambda_i)\varepsilon_{Hb}(\lambda_i)\right)}{\left(\sum_i \varepsilon_{HbO2}^2(\lambda_i)\right)\left(\sum_i \varepsilon_{Hb}^2(\lambda_i)\right) - \left(\sum_i \varepsilon_{HbO2}(\lambda_i)\varepsilon_{Hb}(\lambda_i)\right)^2},$$

$$\Delta[Hb]^* = \frac{\left(\sum_i N''(\lambda_i)\varepsilon_{Hb}(\lambda_i)\right)\left(\sum_i \varepsilon_{HbO2}^2(\lambda_i)\right) - \left(\sum_i N''(\lambda_i)\varepsilon_{HbO2}(\lambda_i)\right)\left(\sum_i \varepsilon_{HbO2}(\lambda_i)\varepsilon_{Hb}(\lambda_i)\right)}{\left(\sum_i \varepsilon_{HbO2}^2(\lambda_i)\right)\left(\sum_i \varepsilon_{Hb}^2(\lambda_i)\right) - \left(\sum_i \varepsilon_{HbO2}(\lambda_i)\varepsilon_{Hb}(\lambda_i)\right)^2}$$

and where OL is the oxygenation level of the tumor; i is a wavelength index for the two wavelengths; $\varepsilon_{HbO2}$ and $\varepsilon_{Hb}$ are the molar extinction coefficients of oxy-hemoglobin and deoxy-hemoglobin, respectively; $\Delta[HbO_2]^*$ and $\Delta[Hb]^*$ are relative values for the spatial changes in the concentrations of oxy-hemoglobin and deoxy-hemoglobin, respectively; and N" is a spatial second derivative of an intensity of transmitted light.

These methods can include one or more of the following features. The sample may be illuminated with a plurality of wavelengths of light, and the light transmitted through the sample may be detected at a plurality of locations. An image of oxygenation levels at the plurality of locations within the tissue sample may be displayed. Values of oxygenation levels at the plurality of locations within the tissue sample may be stored in a computer-readable medium.

In another aspect, the invention features methods for diagnosing cancer in a sample by obtaining thicknesses of the sample and intensities of light transmitted through the sample at two or more locations; calculating data points for the locations using spatial second derivatives of products of the thickness of the sample and the intensities of the transmitted light; comparing the data points to detect a region of the sample having an absorption level different from the background level of absorption within the sample; selecting a pair of wavelengths of light to minimize the difference between relative changes in intensity of the light transmitted through the region of the sample, where the relative changes in intensity of the light are measured relative to the background intensity of light transmitted through the sample; obtaining measures of background reduced scattering coefficients of the sample at the pair of wavelengths; calculating an absolute oxygenation level of the region of the sample using the relative changes in intensity of the light at the pair of wavelengths and the measures of the background reduced scattering coefficients of the sample at the pair of wavelengths; and diagnosing whether the region of the sample contains cancer based on the absolute oxygenation level of the region.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF DRAWINGS

FIGS. 24a1 to 24c2 are a series of images of a ductal carcinoma in a left breast.

FIGS. 25a to 25c are a series of images of a benign mastopathy in a left breast.

Like reference symbols in the various drawings indicate like elements.

DETAILED DESCRIPTION

The invention features optical systems and methods for imaging based on oxygenation levels and quantifying oxygenation levels within a region of interest. These systems and methods are useful to assess differences in oxygenation levels within mammalian, human, e.g., tissue and have particular application to identifying cancerous tumors in breast tissue in vivo. The imaging techniques provide enhanced contrast by mapping the second derivative of the optically acquired data. Measurement of absolute oxygenation levels involves selection of an appropriate pair of wavelengths to minimize the difference between the relative change in the intensity of the light detected at those wavelengths.

Optical Systems

Figure 1:
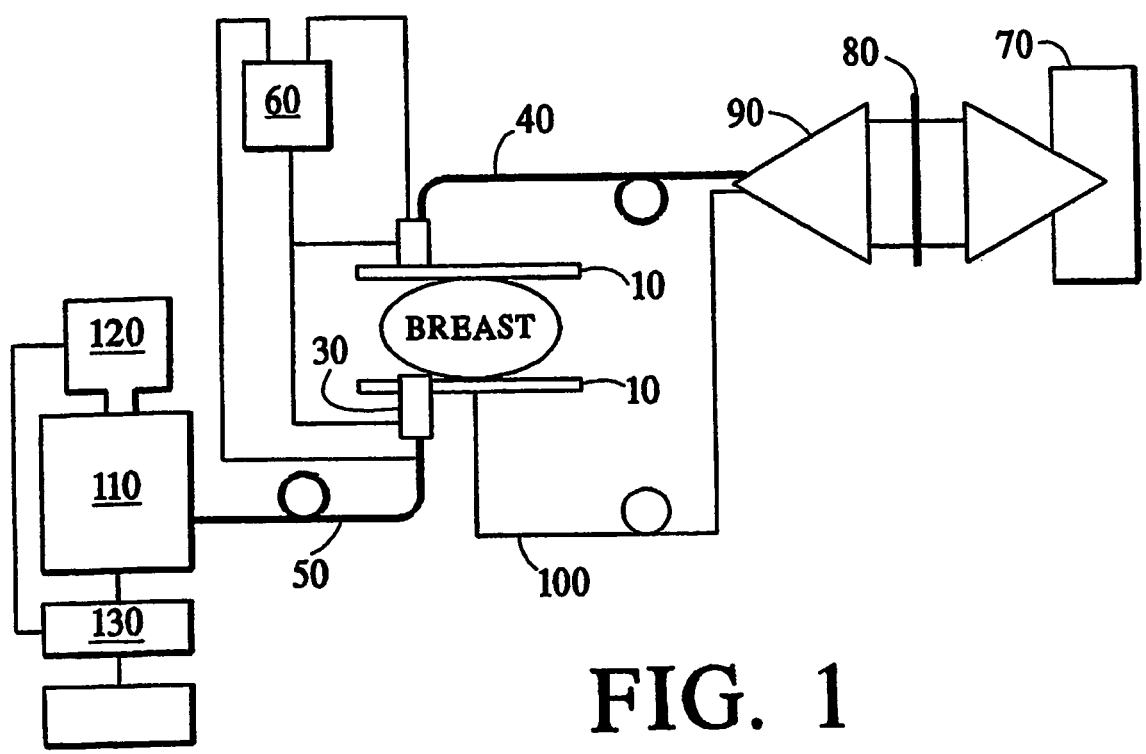
FIG. 1 is a schematic diagram of a system of the present invention.

An optical system for scanning a human breast according to the present invention is shown in FIG. 1. Two glass plates 10 are used to slightly compress the breast. Two distance sensors 20 and 30 positioned next to the illumination 40 and collection fibers 50 measure the free space between the compression plates and the breast. The difference between the plate separation and this free space yields the breast thickness at each pixel. The distance between the two plates is adjustable to fit different breast sizes, and it is possible to rotate the whole assembly to allow for the acquisition of breast images in the craniocaudal, oblique, and mediolateral projections. The output of the distance sensors (or, as an alternative, the optical signal detected by the scanning collection fiber 50) is also used to detect the proximity to the breast edge. By driving the scanner to the next line using the driving circuit 60 when the detected breast thickness becomes less than 1 cm (or when the optical transillumination signal through the breast exceeds a given threshold), the system only scans the area actually occupied by the breast.

The light source can be a Xe arc lamp 70 (ORIEL Instruments, Model No. 6258), and the light is passed through a band-pass filter 80 to emit over the spectral range 680-880 nm. This continuous wave (CW) light source provides a complete range for selection of optimal wavelengths. The lamp 80 is coupled through a F/1.0 condenser and a converging lens (collectively shown as 90) to either or both of the 3-5 mm diameter glass fiber bundles 40 and 100. A fiber bundle 100, which is a fixed illumination fiber, can be used for background spectroscopy. The collection fiber 50, a fiber bundle with an internal diameter of 3-5 mm and a numerical aperture of 0.22, delivers the light to the entrance slit of a 15 cm-f/4 spectrograph 110 (Roper Scientific, VersArray: 512B) for the parallel measurement of the whole spectrum at each pixel. The CCD camera chip 120 is appropriately binned to achieve the best compromise between signal-to-noise ratio and spectral resolution. The spectral data for the whole image is stored in a computer 130 and is post-processed. A display 140 displays an image of the post-processed data.

Second-Derivative Imaging

Processing optical data from breast tissue using spatial second derivatives further enhances the detection of areas of higher light absorption in the breast. Light absorption is a function of concentration and oxygenation levels. The second-derivative images at multiple wavelengths can be used in spectral analysis, which improves the specificity of optical mammography by discriminating between benign and malignant breast lesions.

Figure 2:
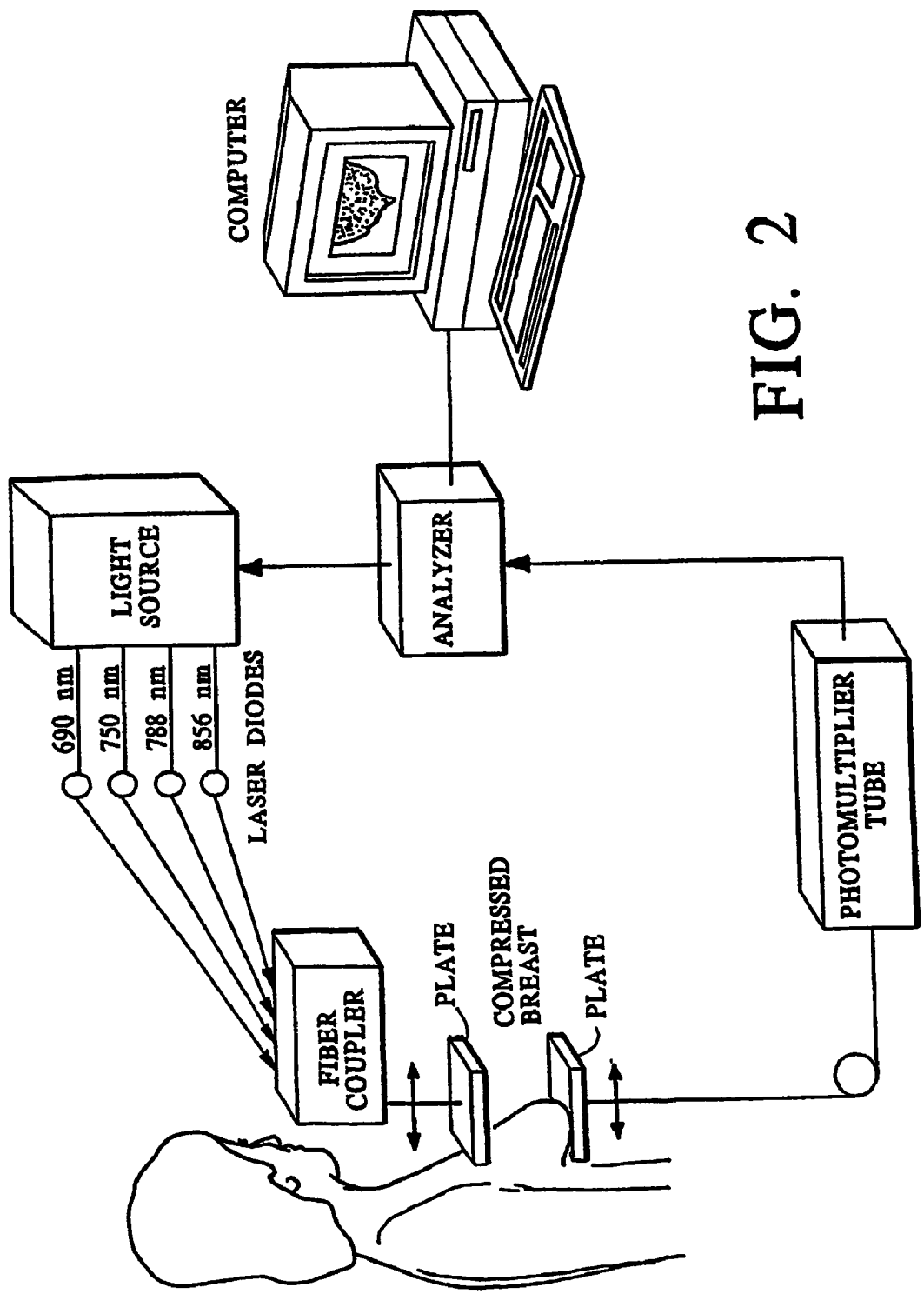
FIG. 2 is a prototype of the new system used to obtain optical data for second-derivative images.
Figure 3:
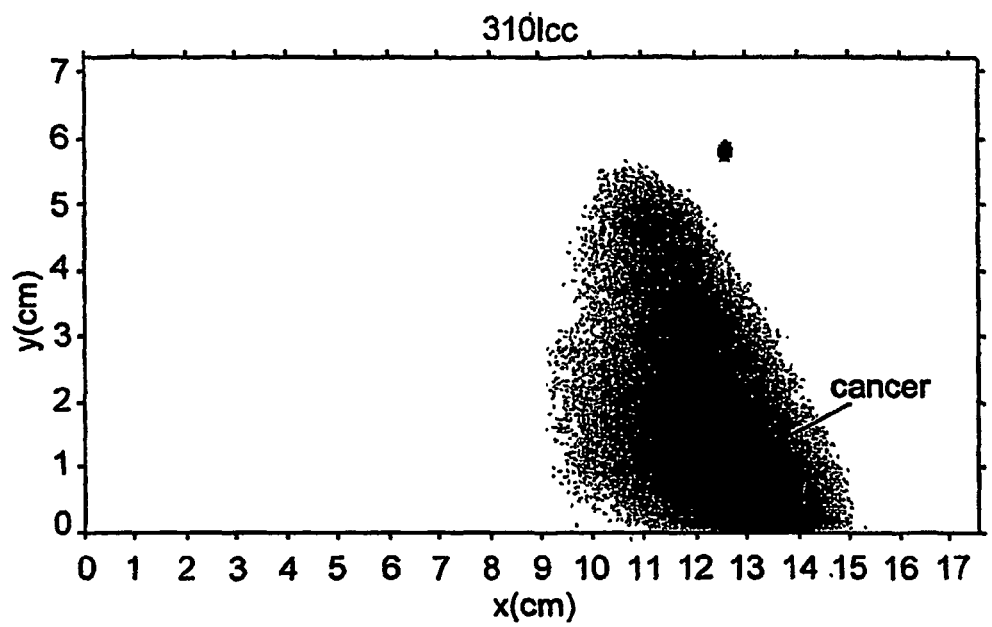
FIG. 3 is a prior art image of the left breast, craniocaudal projection, for a 58-year old patient affected by invasive ductal carcinoma
Figure 4:
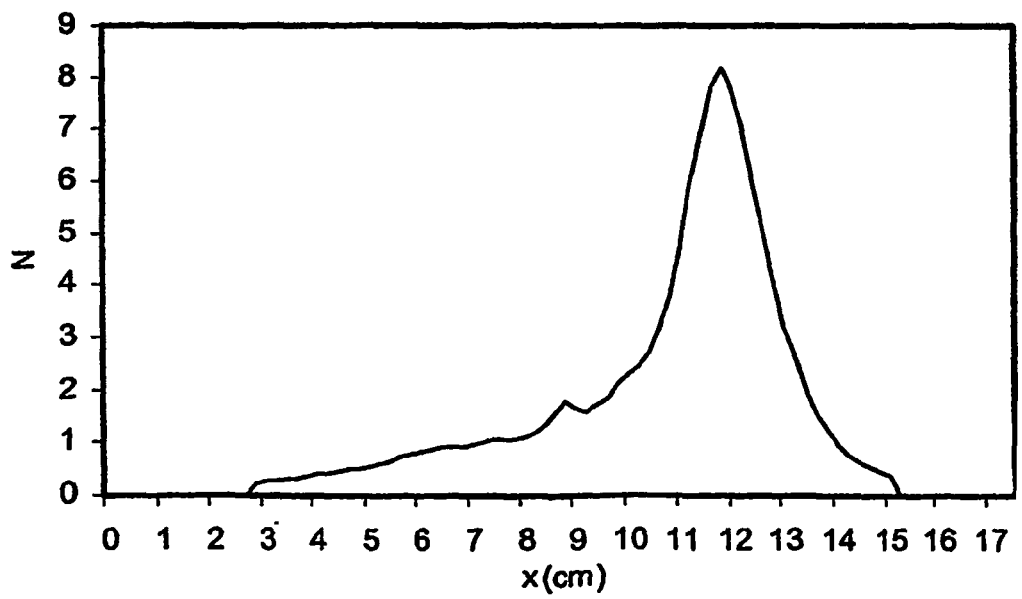
FIG. 4 is a line graph derived from the data shown in FIG. 3 at y=3.2 cm.

Optical data for second-derivative images were acquired using a prototype designed and built by Siemens Medical Engineering (Erlangen, Germany) shown in FIG. 2. Other devices can be used to acquire images. This prototype did not feature a CW light source. Instead, four laser diodes (690, 750, 788, and 856 nm) modulated at a frequency of 70 MHz were used as optical sources. The light from these diodes was fed into optical fibers, which were joined to a fiber coupler. The source and detector fibers are located on opposite sides of the breast, which was slightly compressed between two parallel glass plates. The light received from the detector fibers passed through a photomultiplier tube and analyzer to a computer. Amplitude and phase images were obtained by scanning the source and detector fibers in tandem. Two projections of each breast were typically acquired, craniocaudal and oblique. The raw data was corrected for edge effects arising from the variable thickness of the breast between the two plates. The edge-corrected data yield was used to create images based on an N-parameter, defined as $N(x,y)=r_0 ac_0/r(x,y)ac(x,y)$, where $r_0$ is the maximum thickness of the sample, $ac_0$ is the AC amplitude at a pixel where the breast thickness is $r_0$, $ac(x,y)$ is the amplitude measured at pixel $(x,y)$, and $r(x,y)$ is the breast thickness at that pixel derived from the phase information, see S. Fantini et al., Med. Phys. 23:149-57, 1996. A representative N-image of the left breast, craniocaudal projection, for a 58-year old patient affected by invasive ductal carcinoma is reported in FIG. 3. A line graph of N at y=3.2 cm is shown in FIG. 4.

Figure 5:
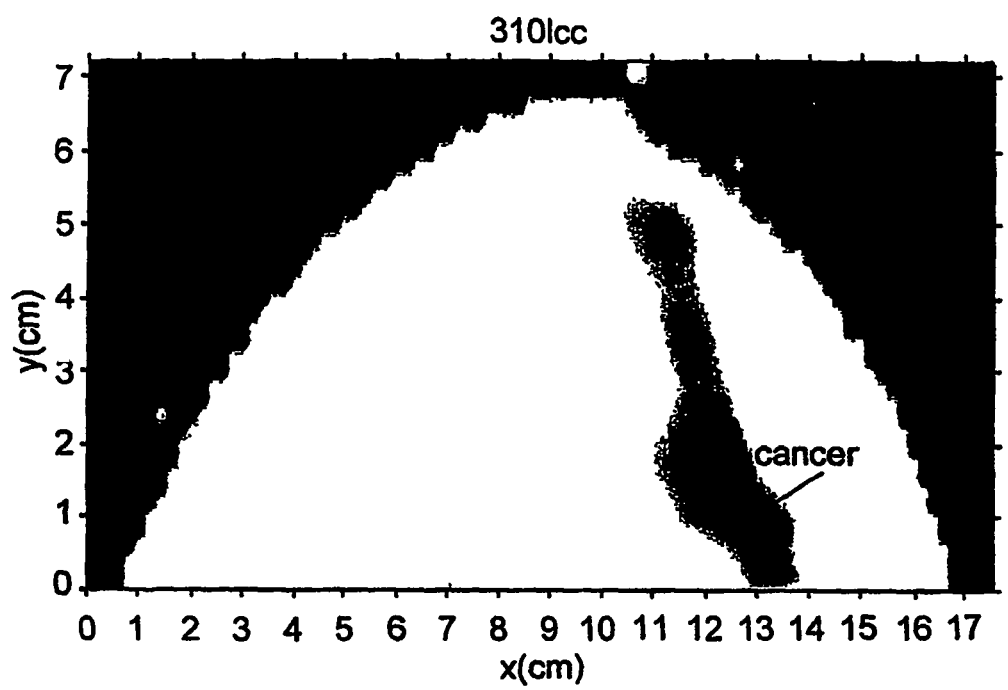
FIG. 5 is second-derivative image of the data generated by the new methods.

FIG. 5 is an image obtained by taking the second derivative (N"). This image was generated by first smoothing the N-image and then taking the sum of the second derivatives at each pixel (i,j) calculated in the vertical (y), horizontal (x), and two (x+y and x−y) diagonal directions, which are defined as follows:

$$N''_{i,j}(x) = \frac{N_{i+1,j} - 2N_{i,j} + N_{i-1,j}}{(\Delta_i)^2},$$

$$N''_{i,j}(y) = \frac{N_{i,j+1} - 2N_{i,j} + N_{i,j-1}}{(\Delta_j)^2},$$

$$N''_{i,j}(x+y) = \frac{N_{i+1,j+1} - 2N_{i,j} + N_{i-1,j-1}}{(\Delta_i)^2 + (\Delta_j)^2},$$

$$N''_{i,j}(x-y) = \frac{N_{i+1,j-1} - 2N_{i,j} + N_{i-1,j+1}}{(\Delta_i)^2 + (\Delta_j)^2},$$

where i and j are the pixel indices in the x and y directions, respectively, while $\Delta_i$ and $\Delta_j$ are the pixel size in the x and y directions, respectively. Alternatively, instead of the sum one can take the maximum value of the second derivative.

Figure 6:
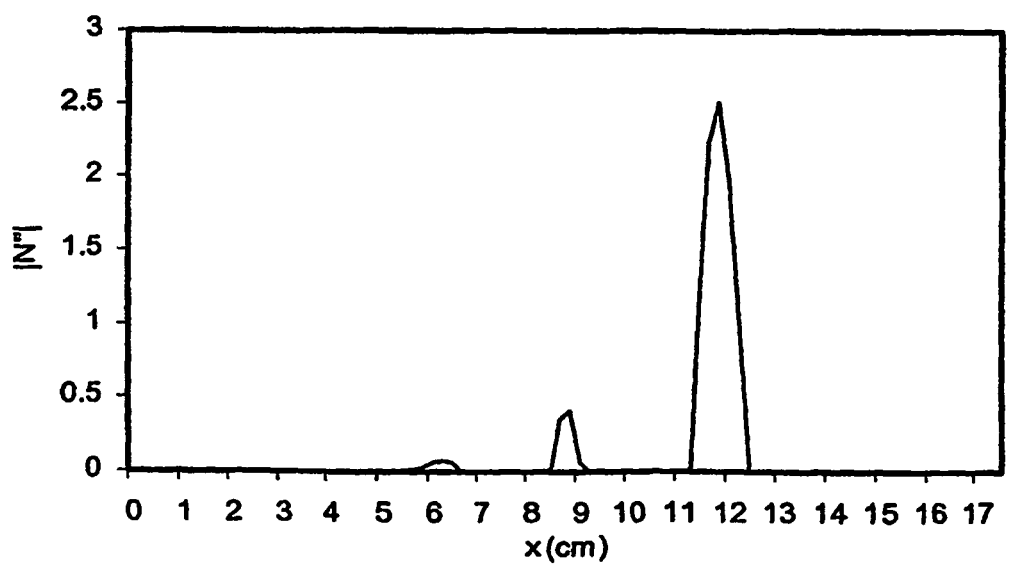
FIG. 6 is a line graph derived from the data shown in FIG. 5 at y=3.2 cm.

FIG. 6 shows a line graph of N" at y=3.2 cm. In FIG. 5, areas with positive N" are set to white (by setting a threshold at N"=0), areas with negative N" (corresponding to regions of high optical absorption, and generally indicative of lesions) are displayed in gray-scale, and the region external to the breast is set to black. This image has enhanced contrast and identifies those areas in the image characterized by a local maximum. As FIG. 5 demonstrates, the secondary peak at x=9 cm is now greatly enhanced, and an even smaller feature around x=6 cm is now visible.

Measurement of Oxygenation Levels

Figure 7:
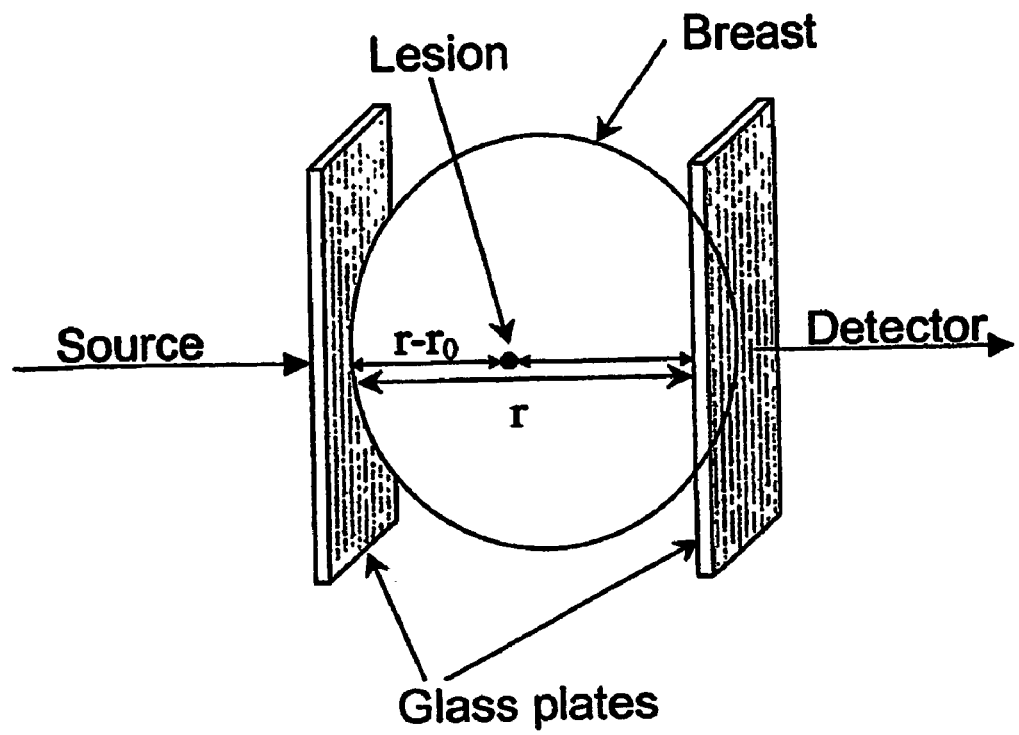
FIG. 7 is a schematic diagram of a breast slightly compressed between two parallel plates.

To a first approximation, a localized optical perturbation embedded in a turbid medium can be modeled using the first-order perturbative solution to the diffusion equation. First-order perturbation applies to small optical perturbations, where "small" means that the linear dimensions of the perturbation are much smaller than the distance r between the illumination and the collection points that induce a small (with respect to 1) relative change in the optical signal. This model is schematically illustrated in FIG. 7 for a lesion embedded in a transilluminated human breast, where the lesion is located at a distance $r_0$ from a glass plate on the detector side and at a distance $r-r_0$ from a glass plate on the source side of the breast model.

The absorption and reduced scattering coefficients of the background medium (healthy breast tissue) are denoted with $\mu_{a0}$ and $\Delta\mu_{s0}'$, respectively, and the absorption and scattering perturbations (associated with the tumor) with $\Delta\mu_a$ and $\Delta\mu_s'$, respectively. This means that the absorption and reduced scattering coefficients at the location of the optical perturbation (tumor) are given by $\mu_{a0}+\Delta\mu_a$ and $\mu_{s0}'+\Delta\mu_s'$, respectively. The relative intensity change $\Delta I/I_0$ (where $I_0$ is the unperturbed intensity measured in the background medium) induced by the optical perturbation is maximized (in absolute value) when the source, detector, and the perturbation are collinear as shown in FIG. 7. The first-order perturbative solution to the diffusion equation leads to the following expression for this maximal intensity change, see Boas et al., Appl. Opt. 36:75-92, 1997, which is incorporated by reference herein:

$$\left.\frac{\Delta I^{(pert)}}{I_0}\right|_{max} = -\left(\frac{3\mu_{s0}'}{4\pi}\right) \quad (1)$$

$$\frac{rV}{r_0(r-r_0)}\left[\Delta\mu_a + \frac{\Delta\mu_s'}{3\mu_{s0}'^2}\left(\sqrt{3\mu_{a0}\mu_{s0}'} + \frac{1}{r_0}\right)\left(\sqrt{3\mu_{a0}\mu_{s0}'} + \frac{1}{(r-r_0)}\right)\right]$$

V is the volume of the lesion, and the geometrical parameters r and $r_0$ are defined in FIG. 7. The second term inside the square bracket in Eq. (1), the scattering perturbation term, is neglected on the basis of in vivo studies that have shown that the scattering tumor-to-background contrast is much smaller than the absorption contrast, see, e.g., Fantini et al., App. Opt. 37:1982-89, 1998, which is incorporated herein by reference. Therefore, Eq. (1) reduces to:

$$\left.\frac{\Delta I^{(pert)}}{I_0}\right|_{max} = -\left(\frac{3rV}{4\pi r_0(r-r_0)}\right)(\mu_{s0}'\Delta\mu_a) \quad (2)$$

As shown by Eq. (2), first-order perturbation theory predicts that the maximal intensity effect of an optical inclusion (for the case $\Delta\mu_s'=0$) is given by the product of a wavelength-independent geometric factor and a wavelength-dependent factor given by $\mu_{s0}'\Delta\mu_a$.

In the new oximetry techniques, Eq. (2) is generalized to predict the functional dependence of $\Delta I/I_0|_{max}$ on $\mu_{a0}$, $\mu_{s0}'$ and $\Delta\mu_a$ beyond the limits of validity of the first-order perturbation analysis. Specifically, in the case $\Delta\mu_s'=0$, Eq. (2) is generalized to the case of spatially extended objects that induce significant changes in the optical intensity. This is accomplished by expressing $\Delta I/I_0|_{max}$ only as a function of the product $\mu_{s0}'\Delta\mu_a$, and wavelength-independent parameters that are related to the source-detector separation (r), and to the object-detector distance ($r_0$), size (V), and shape (s) of the object. Therefore, $\Delta I/I_0|_{max}$ can be expressed as:

$$\left.\frac{\Delta I}{I_0}\right|_{max} = f(r, r_0, V, s, [\mu_{s0}'\Delta\mu_a]) \quad (3)$$

where f indicates an unknown function of its arguments.

As in the perturbation case, $\Delta I/I_0|_{max}$ is a monotonic function of the product $\mu_{s0}'\Delta\mu_a$. The wavelength dependence of $\Delta I/I_0|_{max}$ only appears implicitly in the argument $\mu_{s0}'\Delta\mu_a$, because the geometrical parameters r, $r_0$, V, and s are independent of the wavelength. Consequently, because of the monotonicity of $\Delta I/I_0|_{max}$ on $\mu_{s0}'\Delta\mu_a$, if two wavelengths $\lambda_1$ and $\lambda_2$ are selected such that $\Delta I/I_0|_{max}^{(\lambda_1)}=\Delta I/I_0|_{max}^{(\lambda_2)}$, then $\mu_{s0}'(\lambda_1)\Delta\mu_a(\lambda_1)=\mu_{s0}'(\lambda_2)\Delta\mu_a(\lambda_2)$. Therefore, the ratio of the absorption perturbations at these two wavelengths is given by the inverse of the ratio of the background reduced scattering coefficients at the same two wavelengths:

$$\frac{\Delta\mu_a(\lambda_2)}{\Delta\mu_a(\lambda_1)} = \frac{\mu_{s0}'(\lambda_1)}{\mu_{s0}'(\lambda_2)}. \quad (4)$$

This analysis indicates that by appropriately choosing the two wavelengths $\lambda_1$ and $\lambda_2$, one can translate a measurement of the background scattering ratio into a measurement of the absorption-perturbation ratio associated with the embedded inclusion. This result is relevant for the near-infrared determination of the oxygen saturation of hemoglobin in breast lesions because (1) the near-infrared spectral properties of hemoglobin and breast tissue are such that it is usually possible to identify two wavelengths at which the tumor-induced intensity perturbations are similar, and because (2) the oxygen saturation of hemoglobin is only a function of the ratio of the optical absorption at two wavelengths, see Fantini et al., Opt. Eng., 34:32-42, 1995. If the absorption at the tumor location is given by the sum of the contributions from the background ($\mu_{a0}$) and from the tumor ($\mu_a^{(t)}$), then $\Delta\mu_a$ can be identified with the tumor absorption ($\mu_a^{(t)}=\Delta\mu_a$. If, instead, the absorption at the tumor location is only due to the tumor, then $\mu_a^{(t)}=\mu_{a0}+\Delta\mu_a$. However, if $\Delta\mu_a>>\mu_{a0}$ (high-contrast tumor), it can still be maintained that $\Delta\mu_a$ is representative of the tumor absorption ($\mu_a^{(t)}\approx\Delta\mu_a$).

Here, the oxygen saturation of hemoglobin ($SO_2$) associated with the additional absorption $\Delta\mu_a$ is considered. At least in the two cases mentioned above, $SO_2$ is representative of the tumor oxygenation. By assuming that $\Delta\mu_a$ is solely due to hemoglobin, the expression for $SO_2$ in terms of $\Delta\mu_a(\lambda_1)$ and $\Delta\mu_a(\lambda_2)$ becomes the following:

$$SO_2 = \frac{\varepsilon_{Hb}(\lambda_2) - \varepsilon_{Hb}(\lambda_1)\Delta\mu_a(\lambda_2)/\Delta\mu_a(\lambda_1)}{[\varepsilon_{Hb}(\lambda_2) - \varepsilon_{HbO2}(\lambda_2)] + [\varepsilon_{HbO2}(\lambda_1) - \varepsilon_{Hb}(\lambda_1)]\Delta\mu_a(\lambda_2)/\Delta\mu_a(\lambda_1)}, \quad (5)$$

where $\varepsilon_{Hb}$ and $\varepsilon_{HbO2}$ are the molar extinction coefficients of deoxy-hemoglobin and oxy-hemoglobin, respectively.

In practice, it may not be possible to identify two wavelengths $\lambda_1$ and $\lambda_2$ that exactly satisfy the requirement that $\Delta I/I_0|_{max}^{(\lambda_1)}=\Delta I/I_0|_{max}^{(\lambda_2)}$. In this case, the optimal pair of wavelengths $(\lambda_1,\lambda_2)$ minimizes the absolute value of the difference $\Delta I/I_0|_{max}^{(\lambda_1)}-\Delta I/I_0|_{max}^{(\lambda_2)}$. To correct, at least in part, for a difference between $\Delta I/I_0|_{max}^{(\lambda_1)}$ and $\Delta I/I_0|_{max}^{(\lambda_2)}$, the dependence $\Delta I/I_0|_{max}^{(\lambda)} \propto \mu'_{s0}(\lambda)\Delta\mu_a(\lambda)$ given by Eq. (2) is used to write:

$$\frac{\Delta\mu_a(\lambda_2)}{\Delta\mu_a(\lambda_1)} = \frac{\mu'_{s0}(\lambda_1)}{\mu'_{s0}(\lambda_2)} \frac{\Delta I/I_0|_{max}^{(\lambda_2)}}{\Delta I/I|_{max}^{(\lambda_1)}}. \quad (6)$$

By combining Eqs. (5) and (6), the lesion saturation is given by:

$$SO_2 = \frac{\varepsilon_{Hb}(\lambda_2) - \varepsilon_{Hb}(\lambda_1)\frac{\mu'_{s0}(\lambda_1)\Delta I/I_0|_{max}^{(\lambda_2)}}{\mu'_{s0}(\lambda_2)\Delta I/I|_{max}^{(\lambda_1)}}}{[\varepsilon_{Hb}(\lambda_2) - \varepsilon_{HbO2}(\lambda_2)] + [\varepsilon_{HbO2}(\lambda_1) - \varepsilon_{Hb}(\lambda_1)]\frac{\mu'_{s0}(\lambda_1)\Delta I/I_0|_{max}^{(\lambda_2)}}{\mu'_{s0}(\lambda_2)\Delta I/I|_{max}^{(\lambda_1)}}}, \quad (7)$$

which is the equation used to quantify the oxygenation level of, e.g., a tumor, from measurements of (1) the background (healthy tissue) reduced scattering coefficient $[\mu_{s0}'(\lambda)]$, and (2) the maximal relative change in the intensity caused by the tumor $(\Delta I/I_0|_{max}^{(\lambda)})$.

This approach is not exclusively based on first order perturbation theory because the criterion to select the two wavelengths $\lambda_1$ and $\lambda_2$ refers to situations that are beyond the limits of applicability of first-order perturbation theory. As a result, even if $\Delta I/I_0|_{max}$ does not show a linear dependence on $\mu_{s0}'\Delta\mu_a$, as predicted by first-order perturbation theory, these methods still provide accurate readings of oxygenation levels, provided that two wavelengths $\lambda_1$ and $\lambda_2$ can be identified such that $\Delta I/I_0|_{max}^{(\lambda_1)} \approx \Delta I/I_0|_{max}^{(\lambda_2)}$.

In addition to seeking a pair of wavelengths that minimize the intensity change induced by the inclusion, it is preferable to use wavelengths that are not too close to one another. The sensitivity of the oxygenation measurement is degraded if the two near-infrared wavelengths are too close to each other, see Sevick et al., Anal. Biochem. 195:330-51, 1991. To avoid this degradation, the criterion that $|\lambda_2-\lambda_1|>x$ can be adopted to guarantee that the minimization of the absolute value of the difference $\Delta I/I_0|_{max}^{(\lambda_1)}-\Delta I/I_0|_{max}^{(\lambda_2)}$ yields an appropriate pair of wavelengths. Possible values of x include, e.g., any distance between and including 40 and 60 nm.

This approach has the potential of being more robust in practical clinical measurements with respect to full reconstruction schemes. The only information used by the new method is (1) the spectrum of the background scattering coefficient, $\mu_{s0}'(\lambda)$, (2) the background intensity, $I_0(\lambda)$, and (3) the maximum intensity change $(\Delta I)_{max}$ caused by the tumor. To best apply this method, the spectral measurements should be conducted at a large number of wavelengths in the range of 680 to 880 nm, for example continuously over this spectral band.

The reduced scattering coefficient of the background medium as a function of wavelength, $\mu_{s0}'(\lambda)$, can be measured by averaging time-resolved measurements at several breast locations. Because of the featureless scattering spectrum, measurements at a few discrete wavelengths $\lambda_1$ can be effectively extrapolated to yield a continuous spectrum of $\mu_{s0}'(\lambda)$, as demonstrated by Bevilacqua et al., Appl. Opt. 39:6498-507, 2000. With respect to the measurement of the background intensity $I_0(\lambda)$ in the presence of a heterogeneous background such as breast tissue, it can be appropriate to consider an average background intensity over a specifically selected breast area rather than the intensity measured at a particular breast location.

It is also possible to use the transmitted light images to provide information concerning the relative oxygenation level of the detected optical inhomogeneities. Multiple second-derivative images taken at different wavelengths may be used to calculate a relative oxygenation index. In particular, pseudo variations in the concentrations of oxy-hemoglobin $(\Delta[HbO_2])$ and deoxy-hemoglobin $(\Delta[Hb]^*)$ may be determined and then combined to calculate a relative oxygenation index according to the following equations:

$$\Delta[HbO_2]* = \frac{\left(\sum_i N''(\lambda_i)\varepsilon_{HbO2}(\lambda_i)\right)\left(\sum_i \varepsilon_{Hb}^2(\lambda_i)\right) - \left(\sum_i N''(\lambda_i)\varepsilon_{Hb}(\lambda_i)\right)\left(\sum_i \varepsilon_{HbO2}(\lambda_i)\varepsilon_{Hb}(\lambda_i)\right)}{\left(\sum_i \varepsilon_{HbO2}^2(\lambda_i)\right)\left(\sum_i \varepsilon_{Hb}^2(\lambda_i)\right) - \left(\sum_i \varepsilon_{HbO2}(\lambda_i)\varepsilon_{Hb}(\lambda_i)\right)^2}, \quad (8)$$

$$\Delta[Hb]* = \frac{\left(\sum_i N''(\lambda_i)\varepsilon_{Hb}(\lambda_i)\right)\left(\sum_i \varepsilon_{HbO2}^2(\lambda_i)\right) - \left(\sum_i N''(\lambda_i)\varepsilon_{HbO2}(\lambda_i)\right)\left(\sum_i \varepsilon_{HbO2}(\lambda_i)\varepsilon_{Hb}(\lambda_i)\right)}{\left(\sum_i \varepsilon_{HbO2}^2(\lambda_i)\right)\left(\sum_i \varepsilon_{Hb}^2(\lambda_i)\right) - \left(\sum_i \varepsilon_{HbO2}(\lambda_i)\varepsilon_{Hb}(\lambda_i)\right)^2}, \quad (9)$$

$$\text{Oxygenation Index} = \frac{\Delta[HbO_2]*}{\Delta[HbO_2]* + \Delta[Hb]*}. \quad (10)$$

Here, i is the wavelength index, and $\varepsilon_{HbO2}$ and $\varepsilon_{Hb}$ are the molar extinction coefficients of oxy-hemoglobin and deoxy-hemoglobin, respectively. The stars in $\Delta[HbO_2]^*$ and $\Delta[Hb]^*$ refer to indicative (or pseudo) values for the spatial changes in the concentrations of oxy-hemoglobin and deoxy-hemoglobin associated with the spatial changes in the optical absorption coefficient $\Delta\mu_a$. The actual spatial changes $\Delta[HbO_2]$ and $\Delta[Hb]$ would be obtained by replacing $N''(\lambda_i)$ with $\Delta\mu_a(\lambda_i)$ in Eqs. (8) and (9). At least in the first-order perturbation limit, it can be shown that there is a direct proportionality between $N''$ and $\Delta\mu_a$, which is the basis for using $N''$ in Eqs. (8) and (9). However, the proportionality between $N''$ and $\Delta\mu_a$ does not hold for the strong perturbation on the optical data caused by relatively large breast tumors. For this reason, stars in $\Delta[HbO_2]^*$ and $\Delta[Hb]$ are used, the ratio of Eq. (10) may be known as a relative oxygenation index rather than oxygen saturation of hemoglobin.

Diagnosing Cancer

The imaging and absolute oxygenation level quantification techniques described herein can be used in various combinations to diagnose the presence of cancer, for example, in human breasts. For example, one can use any one or two of the N,N'', or oxygenation level images, or one can use all three images of a given tissue sample. Combining these techniques, and comparing their results, affords enhanced images supported by quantitative measurements that improve diagnostic potential.

Optical mammography of human breasts is performed using a system such as that shown in FIG. 2. Two projections of each breast are typically acquired, craniocaudal and oblique, by illuminating the breasts with multiple wavelengths, preferably with at least some of the wavelengths in the range of 680 to 880 nm. Amplitude and phase images are obtained by scanning the source and detector fibers in tandem, and the raw data was corrected for edge effects arising from the variable thickness of the breast between the two plates. Second-derivative images such as FIG. 5 are generated for each breast. These images display differences in light absorption with enhanced contrast, and inclusions with high absorption, such as lesions, can be identified. For example, in FIG. 5, the feature located at x=12 cm is a lesion that represents a region of interest.

The oxygenation levels in the identified regions of interest are quantitatively assessed. To perform the quantitative assessment, a pair of wavelengths is selected to minimize the intensity change induced by the region of interest. Since it is preferable to use wavelengths that are not too close to one another, a boundary condition of, e.g., 40 nm of separation in the two wavelengths is applied. Using these two wavelengths, Eq. (7) is applied to compute the absolute oxygenation level within the region of interest. This absolute oxygenation level improves the ability to distinguish between malignant and benign inclusions. Because measurements of the partial pressure of oxygen in tumors have shown that hypoxic or anoxic conditions often exist in malignant tumors, but not in benign lesions, a low oxygenation level of the region of interest is an indicator of its malignancy. Differences of 5% to 15% in oxygenation levels between normal and malignant tissue have been observed, see, M. J. Holboke et al., J. of Biomed. Opt. 5, 237-247, 2000; Tromberg et al., Neoplasia 2, 26-40, 2000; Tromberg et al., Philos. Trnas. R. Soc. London 352, 661-668, 1997.

The invention is further described in the following examples, which do not limit the scope of the invention described in the claims.

EXAMPLES

Test Samples and Apparatus

Inclusions were comprised of a mixture of General Electric silicones, model No. RTV615 (clear) and model No. RTV11 (white). The white silicone was used as the scattering material and black India ink was used as the absorber. Two different mixtures were prepared with different optical properties, (the first with $\mu_a$~0.05-0.06 cm$^{-1}$ and $\mu_s$'~9-10 cm$^{-1}$ and the second with $\mu_a$~0.11-0.15 cm$^{-1}$ and $\mu_s$'~9-10 cm$^{-1}$ over the wavelength range of 752-840 nm considered) to cover a range of $\Delta\mu_a$ that is representative of the expected absorption contrast of breast lesions in vivo.

Figure 8:
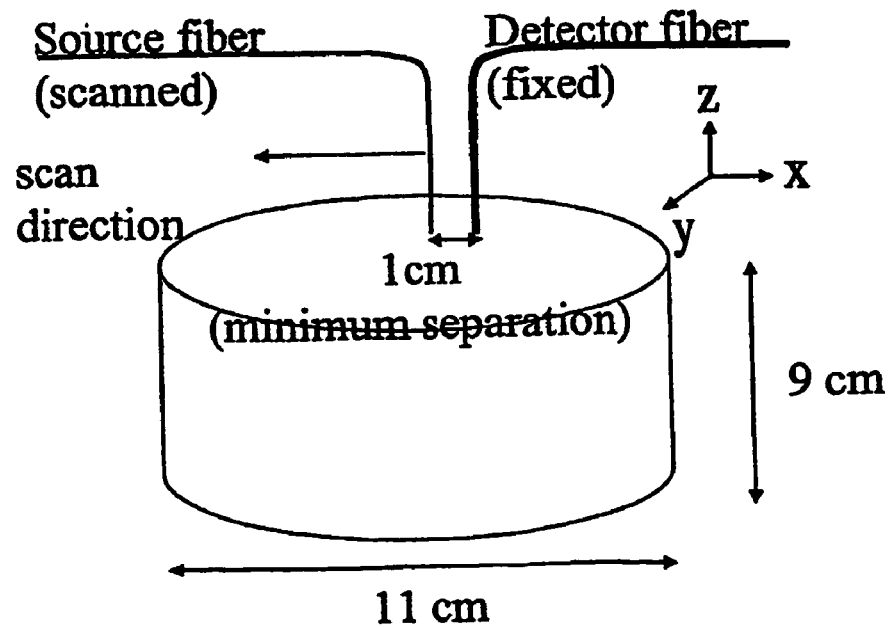
FIG. 8 is a schematic diagram of an optical arrangement for evaluating optical properties in test samples.

The optical characterization of the inclusions was performed using the arrangement shown in FIG. 8. The silicone mixtures were formed into two cylindrically shaped blocks (one to characterize each mixture) of 11 cm diameter and 9 cm height. A frequency-domain, near-infrared spectrometer (OxiplexTS, ISS, Inc., Champaign, Ill.) housed and controlled the laser sources and optical detectors used to obtain the measurements. The sources were laser diodes at six discrete wavelengths (752, 778, 786, 813, 830, and 840 nm) and the optical detector was a photomultiplier tube (Hamamatsu Photonics R928). The sources were intensity-modulated at a frequency of 110 MHz, electronically multiplexed at a rate of about 10 Hz to time-share the detector, and were coupled to 400 μm core-diameter optical fibers that were collected into a fiber bundle with rectangular cross-section 1.2 mm in width and 3 mm in length. The detector was coupled to another fiber bundle of circular cross-section, 3 mm internal diameter. The detector fiber bundle remained fixed and was in contact with the surface of the silicone blocks, while the end of the source bundle was brought close to the surface of the blocks (<0.25 mm away). The starting distance between the source and detector fibers was 1 cm (x-direction). The source fiber was then moved in the negative x-direction defined in FIG. 8 (away from the detector fiber) at a rate of 0.65 mm/s. Data was acquired at every 0.5 s providing a measurement every 325 μm over a total traveled distance of 2 cm. The amplitude (AC), average value (DC), and phase of the detected modulated intensity were recorded and translated into measurements of the reduced scattering and absorption coefficients by employing a multi-distance method based on the diffusion equation and semi-infinite boundary conditions, see Fantini et al., J. Opt. Soc. Am. 11:2128, 1994, which is incorporated herein by reference.

The background medium was comprised of a mixture of 1 liter of Liposyn 10% (Abbott Laboratories, North Chicago, Ill.) and 8 liters of deionized water and was contained in a rectangular vessel with dimensions of 27 cm width, 32 cm length, and 13 cm height. Again, the ISS frequency-domain spectrometer was used to perform the measurements. The experimental arrangement was similar to that used in FIG. 8 except the ends of the source and fiber bundles were fully immersed in the Liposyn mixture to simulate an infinite medium. Acquisition times, laser multiplexing rate and source-displacement speed (with the detector remaining fixed) were also the same as in the inclusion characterization. The AC, DC and phase data were used in the diffusion model for light propagation in an infinite, highly scattering medium to determine the background reduced scattering ($\mu_{s0}$') and absorption coefficients ($\mu_{a0}$). Measurements of $\mu_{a0}$ over the wavelengths used ranged from 0.02 cm$^{-1}$ to 0.04 cm$^{-1}$ and those of $\mu_{s0}$' ranged from 10 cm$^{-1}$ to 12 cm$^{-1}$ and were chosen to match typical absorption and scattering coefficients in breast tissue for this wavelength range [$\mu_a$(breast)~0.03 cm$^{-1}$ and $\mu_s$'(breast)~12 cm$^{-1}$], see Heusmann et al., J. Biomed Opt. 1:425-34, 1996; Heusman et al., Proc. SPIE 2389:788-808, 1995; Kölzer et al., Proc. SPIE 2326:143-52, 1995.

Figures 9, 10:
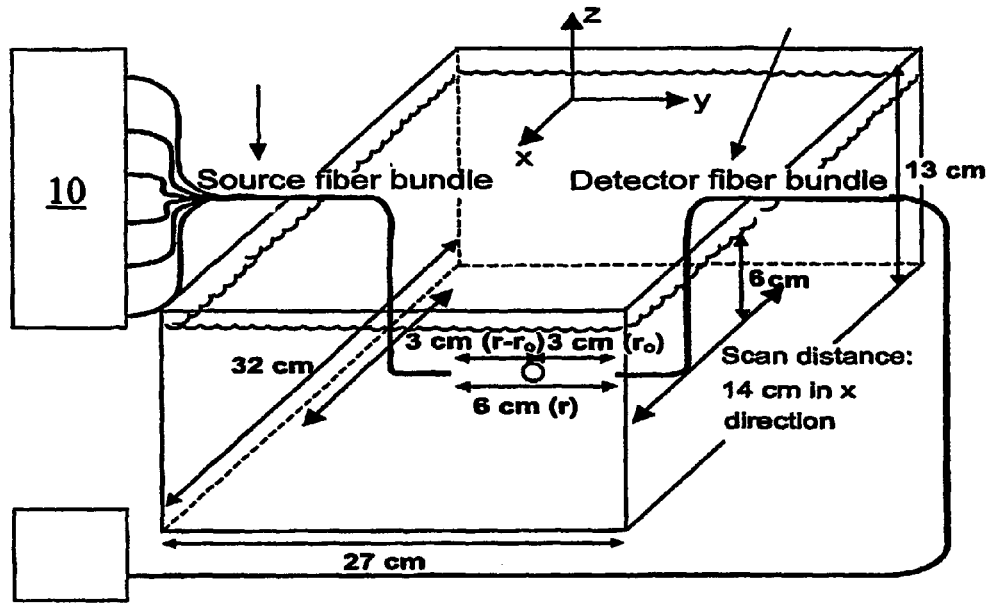
FIG. 9 is a diagram of an apparatus for measuring optical signals in test samples.
FIG. 10 is a table of the results of the measurements of the optical properties of inclusions and background medium in a test sample.

The experimental procedure to investigate the dependence of $\Delta I/I_0|_{max}$ on $\mu'_{s0}\Delta\mu_a$ was based on the arrangement shown in FIG. 9. The laser diodes 10 were employed at the same six wavelengths used previously to determine the optical properties of the inclusion material and the background (752, 778, 786, 813, 830, and 840 nm). In this arrangement, the source fiber bundle 20 and detector fiber bundle 30 were arranged collinearly and their ends were fully immersed in the formerly characterized background medium to simulate an infinite geometry. The detector fiber bundle 30 fed the optical signals into the analyzer 40. The source-detector separation for these experiments remained a constant 6 cm, which is representative of the thickness of a slightly compressed breast. Inclusions of different sizes and shapes were then suspended in the medium equidistant from the source and detector using Pasteur pipettes to hold them in place. The pipettes were filled with background medium to reduce the optical perturbation they might cause.

The inclusion material was formed into irregular shapes (by cutting cylindrical shapes with razor blades) and into a 10 cm-long cylinder using the two different mixtures, thus creating two different sets of the same sizes and shapes. The cylinder had a diameter of 1.0 cm, while the irregular shapes were created to have the same volumes as spheres with 0.9 cm diameter (V-0.43 cm$^3$) and 1.4 cm diameter (V=1.31 cm$^3$), respectively. The source and detector optical fibers were scanned together over a 14 cm distance in the x-direction (as shown in FIG. 9) beginning at a distance of approximately 7 cm from the center of the inclusion in the x-direction. Scanning was performed at a rate of 0.65 mm/s and data was acquired every 0.88 s, providing a data point every 572 μm.

Methods

Estimates of the optical signals were calculated using an analytical solution to the diffusion equation for a spherical inclusion embedded in an infinite turbid medium, see Boas et al., Proc. Natl. Acad. Sci. 51:4887-91, 1994. This solution was implemented in a PMI (photon migration imaging) software package developed by D. A. Boas et al. at Massachusetts General Hospital, Charlestown, Mass., as part of publicly available software, http://www.nmr.mgh.harvard.edu/DOT/toolbox.htm. Two types of theoretical analysis were performed.

The first analysis was aimed at determining whether the dependence of $\Delta I/I_0|_{max}$ on $\mu_{a0}$, $\mu_{s0}'$, and $\Delta\mu_a$ is well approximated by a function of the product $\mu_{s0}'\Delta\mu_a$ even outside of the perturbation regime, as in the cases of spheres having a diameter that is not much smaller than the source-detector separation and for values of $\Delta\mu_a$ that are not much smaller than $\mu_{a0}$. This assessed whether $\Delta I/I_0|_{max}$, in the case where $\Delta\mu_s'=0$ here, was independent of $\mu_{a0}$ and was not affected by $\mu_{s0}'$ and $\Delta\mu_a$ separately, but only by their product $\mu_{s0}'\Delta\mu_a$. This analysis was carried out for two sphere diameters (1.4 and 3.0 cm) in the case where the sphere is equidistant from the source and detector scanning lines (sphere center is 3.0 cm from either fiber in the collinear case). For the smaller sphere (1.4 cm in diameter), a 1.5-cm off-center position was also analyzed, where the distances from the sphere center to the source and detector fibers were 1.5 and 4.5 cm respectively, in the collinear condition.

The second analysis was aimed at testing the new methods for measuring tumor oxygenation. In this analysis, the background absorption and scattering spectra, $\mu_{a0}(\lambda)$ and $\mu_{s0}'(\lambda)$ respectively, were set equal to typical absorption and reduced scattering spectra for breast tissue. The absorption spectra were determined by combining the absorption contributions from typical concentrations of oxy-hemoglobin (~4.4 μM), deoxy-hemoglobin (~2.7 μM), water (~39.5% v/v), and lipids (~60.5% v/v) in healthy breast tissue, as reported by Quaresima et al., Photochem. Photobiol. 67:4-14, 1998. In the spectral region considered (680-880 nm), $\mu_{a0}$ ranged from 0.023 cm$^{-1}$ (at 680 nm) to 0.076 cm$^{-1}$ (at 880 nm). The background scattering spectrum was estimated from data reported by Cubeddu et al., Appl. Phys. Lett. 74:874-76, 1999, for two healthy human subjects. In the spectral region considered (680-880 nm), $\mu_{s0}'$ ranged from 10.0 cm$^{-1}$ (at 680 nm) to 7.8 cm$^{-1}$ (at 880 nm).

In addition, spherical lesions with no scattering contrast ($\Delta\mu_s'=0$) were also considered with an absorption contrast provided by a hemoglobin concentration of 60 μM (corresponding to $\Delta\mu_a=0.12$ cm$^{-1}$ at 800 nm). As in the first analysis, two sphere diameters (1.4 and 3.0 cm) in the centered case were analyzed (sphere half-way between the source and detector scanning lines), along with one sphere diameter (1.4 cm) in the off-center case (sphere 1.5 cm off-center). The maximum relative change in the optical signal induced by the spherical lesion ($\Delta I/I_0|_{max}$) was calculated at nine wavelengths (680, 720, 730, 758, 768, 776, 800, 840, and 880 nm) as a function of hemoglobin saturation values within the sphere over the range 0-100%. This choice of wavelengths covered the 680-880 nm diagnostic window and included the local maxima and minima in the deoxy-hemoglobin absorption spectrum (730 and 758 nm, respectively) and the local minimum in the oxy-hemoglobin absorption spectrum (680 nm).

Testing of the Method

FIG. 10 shows a table of the results of the measurements of the optical properties of the inclusions and background medium. The range of $\Delta\mu_a$ is from 0.014 cm$^{-1}$ to 0.12 cm$^{-1}$ when considering both silicone mixtures, while the range of $\Delta\mu_s'$ is from -0.5 to -2.8 cm$^{-1}$. Given the background optical properties of the order of 0.02 cm$^{-1}$ for $\mu_{a0}$ and 9 cm$^{-1}$ for $\mu_{s0}'$, the absorption perturbations are about 70-600% of the background absorption, while the scattering perturbations, in absolute value, do not exceed 31% of the background reduced scattering coefficient. These conditions are representative of the range of optical contrast offered by tumors in the human breast in vivo.

Figure 11:
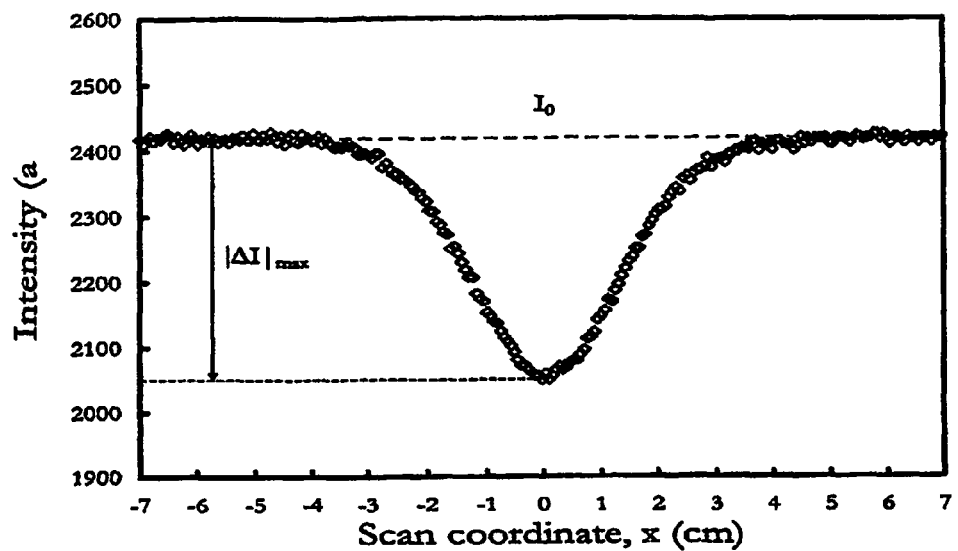
FIG. 11 is a graph of optical intensity (I) measured during a linear scan across a test sample.

FIG. 11 shows a typical result of the optical intensity (I) measured during a linear scan across the object location at x=0. Because $\Delta\mu_a>0$, there is a decrease in detected intensity as the source-detector pair approaches the inclusion during the scan. The background value ($I_0$) and the maximum (in absolute value) intensity change $|\Delta I|_{max}$ are indicated in FIG. 11. The spectrum of $(\Delta I)_{max}/I_0(\lambda)$, is then used to guide the choice of the two wavelengths $\lambda_1$ and $\lambda_2$ that are used to measure the oxygenation of the embedded object according to Eq. (7).

Figure 12:
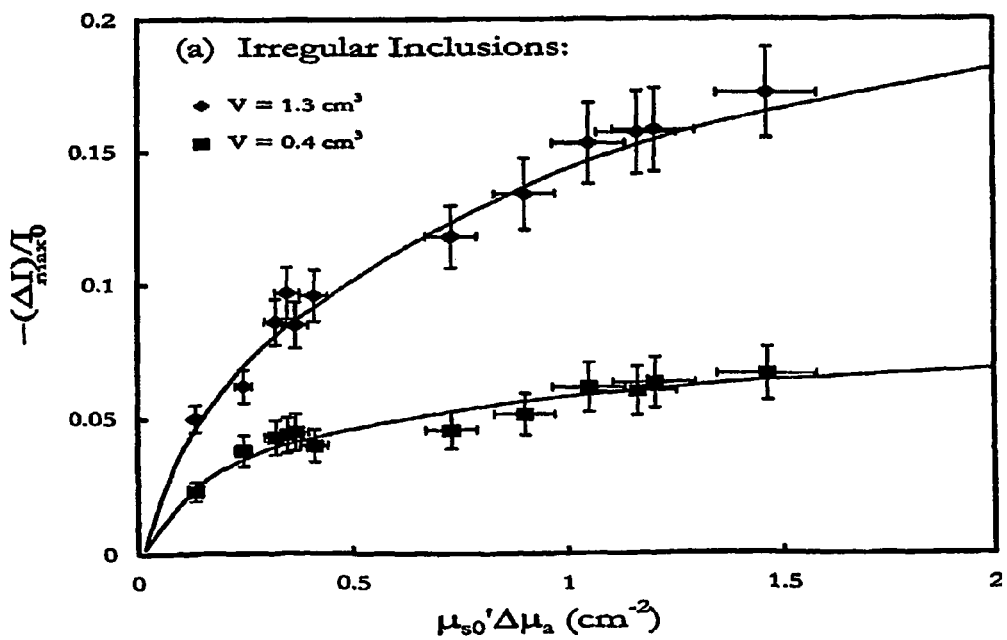
FIG. 12 is a graph of experimental results for $-\Delta I/I_0|_{max}$ as a function of the product $\mu_{s0}'\Delta\mu_a$ for irregularly shaped inclusions in a test sample.
Figure 13:
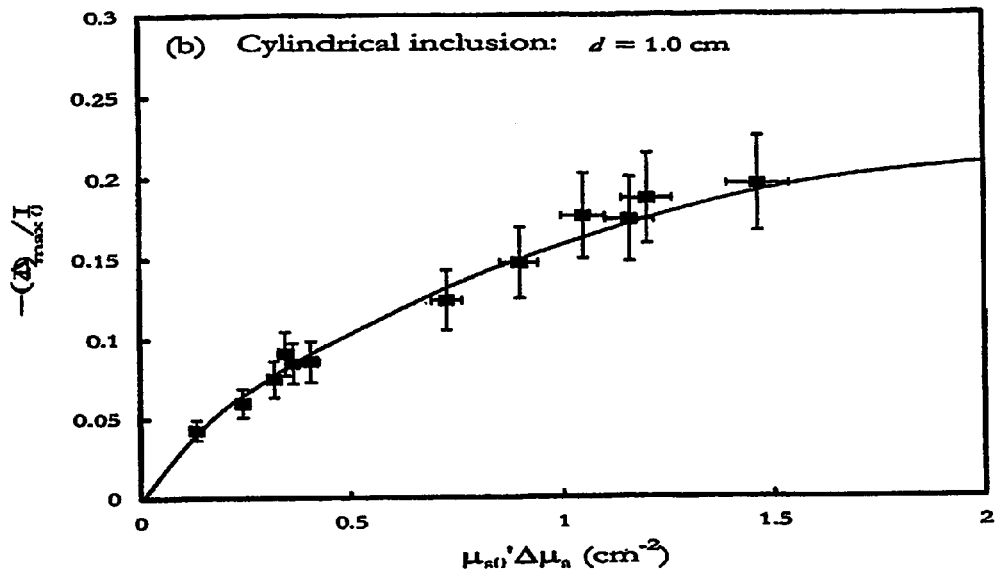
FIG. 13 is a graph of experimental results for $-\Delta I/I_0|_{max}$ as a function of the product $\mu_{s0}'\Delta\mu_a$ for a cylindrical inclusion in a test sample.
Figure 14:
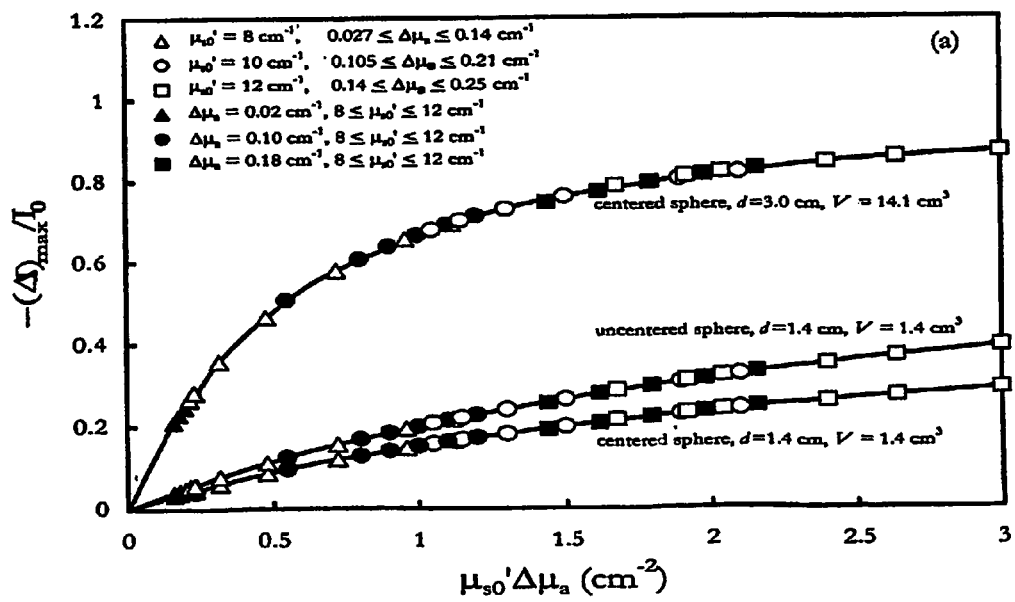
FIG. 14 is the calculated dependence of $-\Delta I/I_0|_{max}$ on the product $\mu_{s0}'\Delta\mu_a$ for a spherical object embedded in a uniform turbid medium.
Figure 15:
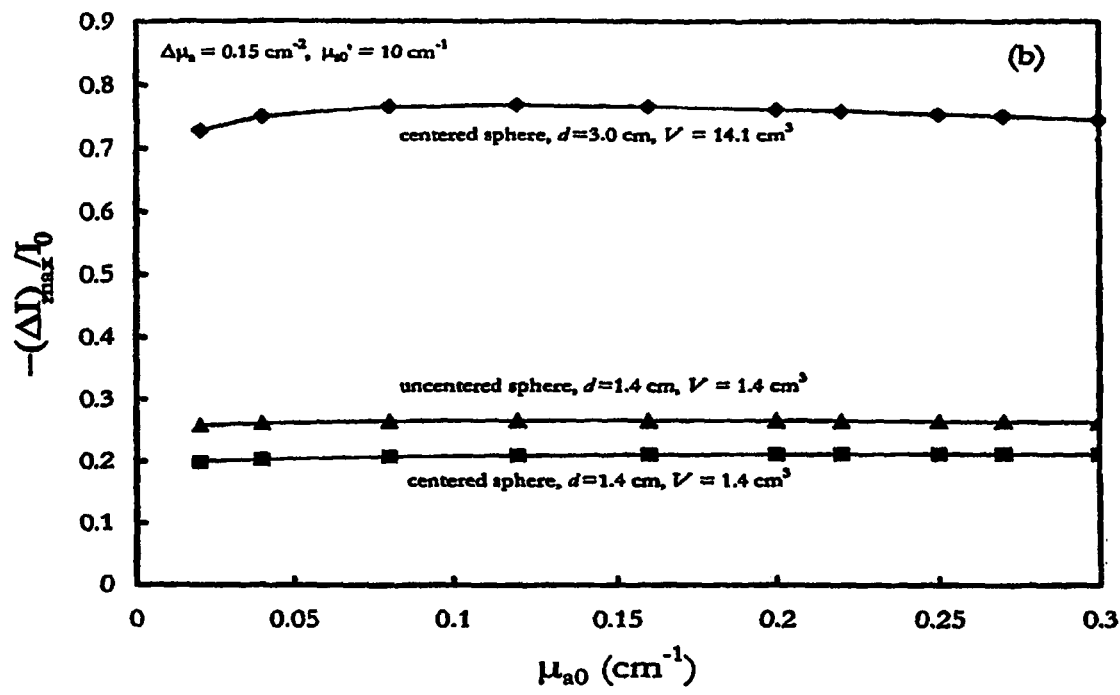
FIG. 15 is a graph showing the dependence of $\Delta I/I_0|_{max}$ on $\mu_{a0}$ for a test sample.

The experimental results for $-\Delta I/I_0|_{max}$ as a function of the product $\mu_{s0}'\Delta\mu_a$ are reported in FIG. 12 for the irregularly shaped inclusions, and in FIG. 13 for the cylindrical inclusion. In both cases, the fact that the experimental data of $\Delta I/I_0|_{max}$ for a range of values of $\mu_{s0}'$ and $\Delta\mu_a$ (see Table 1) are distributed along a single curve as a function of the product $\mu_{s0}'\Delta\mu_a$ is indicative of the dependence of $\Delta I/I_0|_{max}$ on $\mu_{s0}'\Delta\mu_a$. In FIGS. 14 and 15, the functions of $\mu_{s0}'\Delta\mu_a$ are represented by continuous lines. These experiments confirm that $\Delta I/I_0|_{max}$ is only a function of the product $\mu_{s0}'\Delta\mu_a$ even for objects with a relatively large size, cylindrical or irregular shape, and relatively high absorption contrast. Furthermore, $\Delta I/I_0|_{max}$ varies monotonically with $\mu_{s0}'\Delta\mu_a$.

Figure 16:
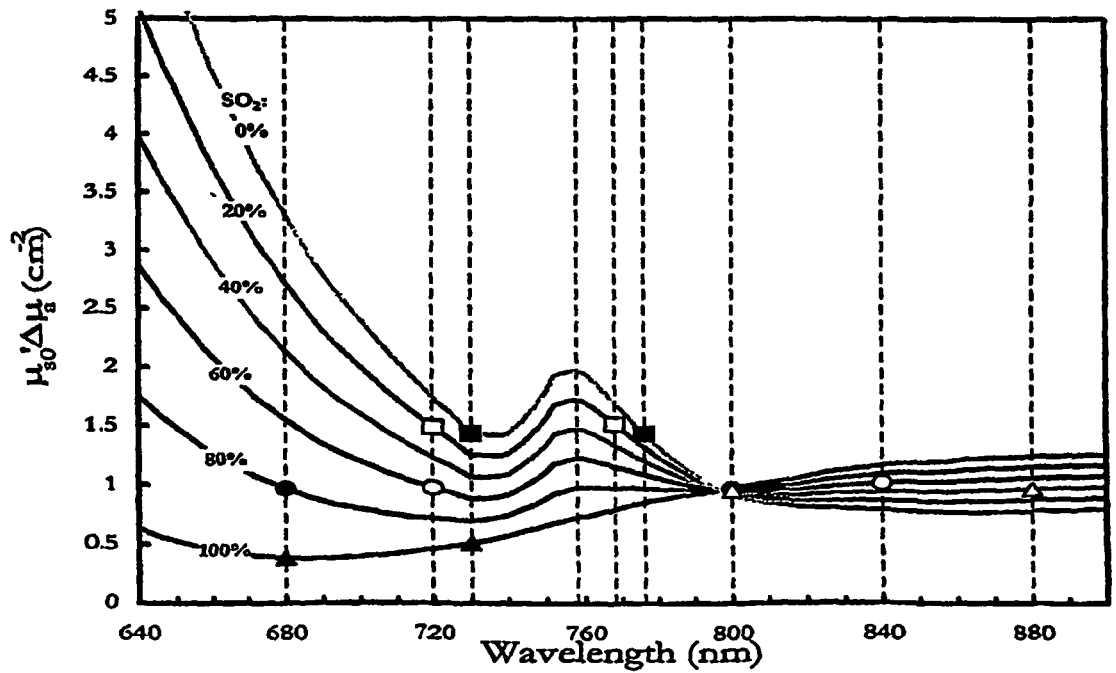
FIG. 16 is a spectrum of the product $\mu_{s0}'\Delta\mu_a$ for $SO_2$ values of 0, 20, 40, 60, 80, and 100%.

FIG. 16 shows the calculated dependence of $-\Delta I/I_0|_{max}$ on the product $\mu_{s0}'\Delta\mu_a$ for a spherical object embedded in a uniform turbid medium. As described above, two spheres (diameters of 1.4 and 3.0 cm) were examined for the case where the sphere was equidistant from the source and detector fibers, and one sphere (diameter of 1.4 cm) for the off-axis case where the sphere was 1.5 cm off the mid-line between source and detector. The absorption coefficient of the background medium ($\mu_{a0}$) is 0.06 cm$^{-1}$, and the scattering perturbation ($\Delta\mu_s'$) was set to zero. In all three cases considered, $\Delta I/I_0|_{max}$ was not separately dependent on $\mu_{s0}'$ and $\Delta\mu_a$, but it only depended, monotonically, on their product (see FIG. 14). Furthermore, FIG. 15 shows that $\Delta I/I_0|_{max}$ was weakly dependent on $\mu_{a0}$ over the range of optical properties of interest.

Computation of Oxygenation Levels

The values of $\Delta I/I_0|_{max}$ at nine wavelengths (680, 720, 730, 758, 768, 776, 800, 840, and 880 nm) were computed for a spherical inclusion in a case that mimics a realistic condition in optical mammography. As described above, the background scattering and absorption spectra were set equal to representative spectra for healthy breast tissue obtained from literature data, see R Cubbedu et al., Appl. Phys. Lett. 74:874-76, 1999; Quaresima et al., Photochem. Photobiol. 67:414, 1998, which are incorporated by reference herein. Because of the results shown in FIG. 15, the background absorption spectrum plays a minor role in the determination of $\Delta I/I_0|_{max}$. The hemoglobin concentration of the embedded lesion was set to a value 60 μM higher than that in the background, and the hemoglobin saturation of the sphere was varied over the range 0-100%.

Figure 17:
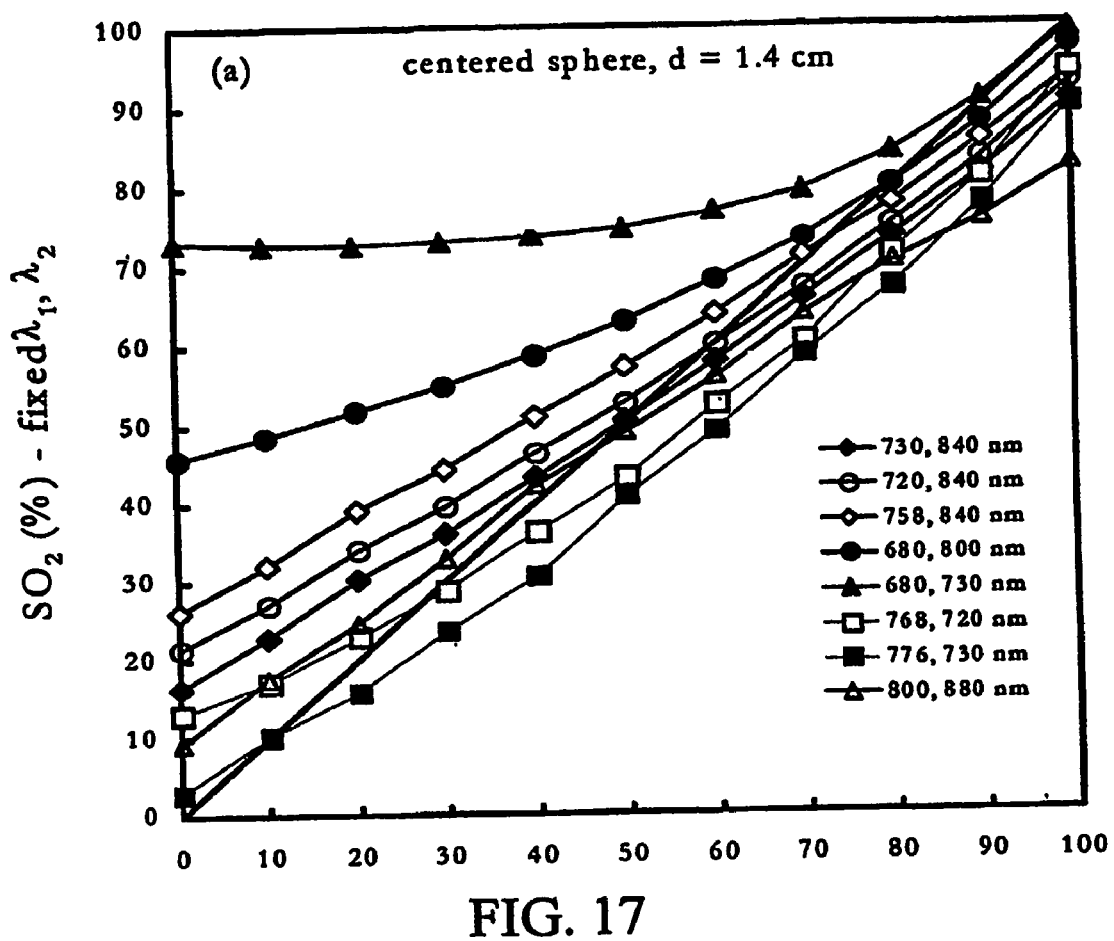
FIG. 17 is graph obtained using prior art perturbation analysis for a number of wavelength pairs for a 1.4 cm-diameter sphere (on the mid-line between source and detector) having a range of oxygenation levels.
Figure 18:
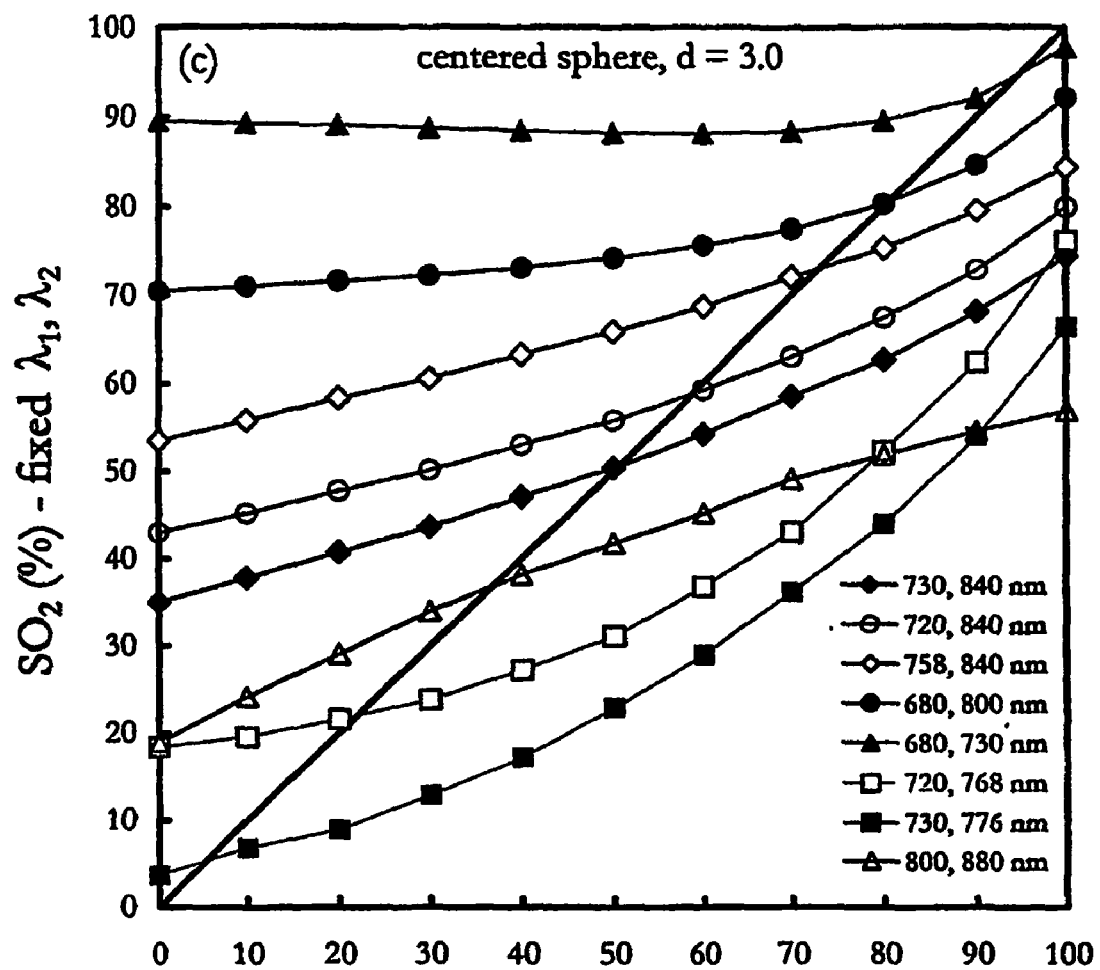
FIG. 18 is graph obtained using prior art perturbation analysis for a number of wavelength pairs for a 3.0 cm-diameter sphere (on the mid-line between source and detector) having a range of oxygenation levels.
Figure 19:
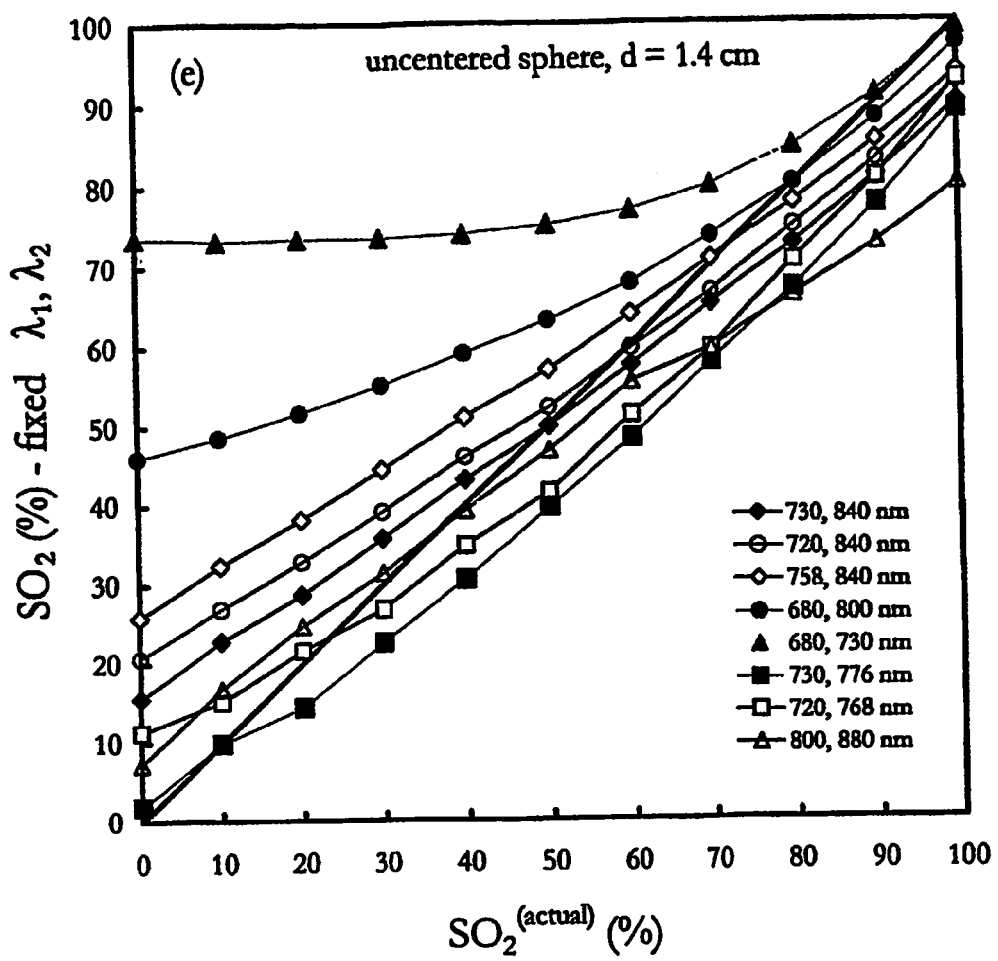
FIG. 19 is graph obtained using prior art perturbation analysis for a number of wavelength pairs for a 1.4 cm diameter sphere (off the mid-line by 1.5 cm) having a range of oxygenation levels.
Figure 20:
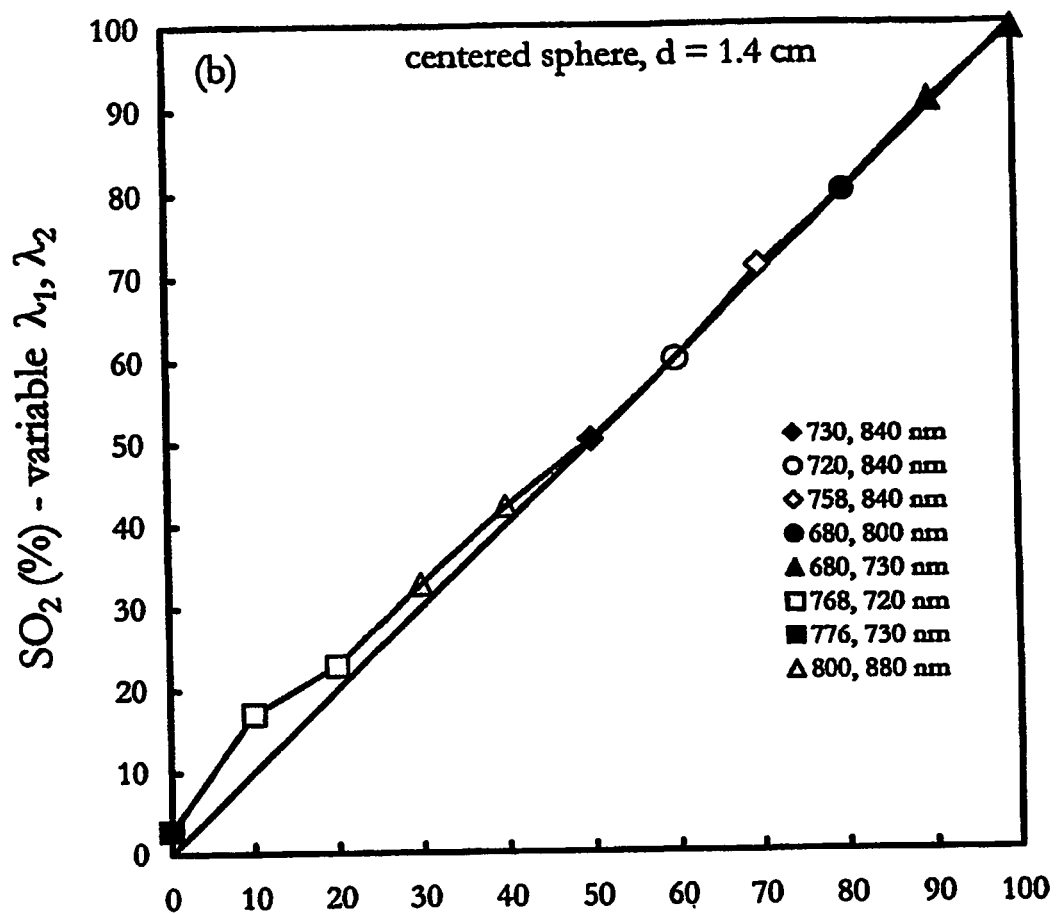
FIG. 20 is a graph obtained using the new methods for a selected wavelength pair for a 1.4 cm-diameter sphere (on the mid-line between source and detector) having a range of oxygenation levels.
Figure 21:
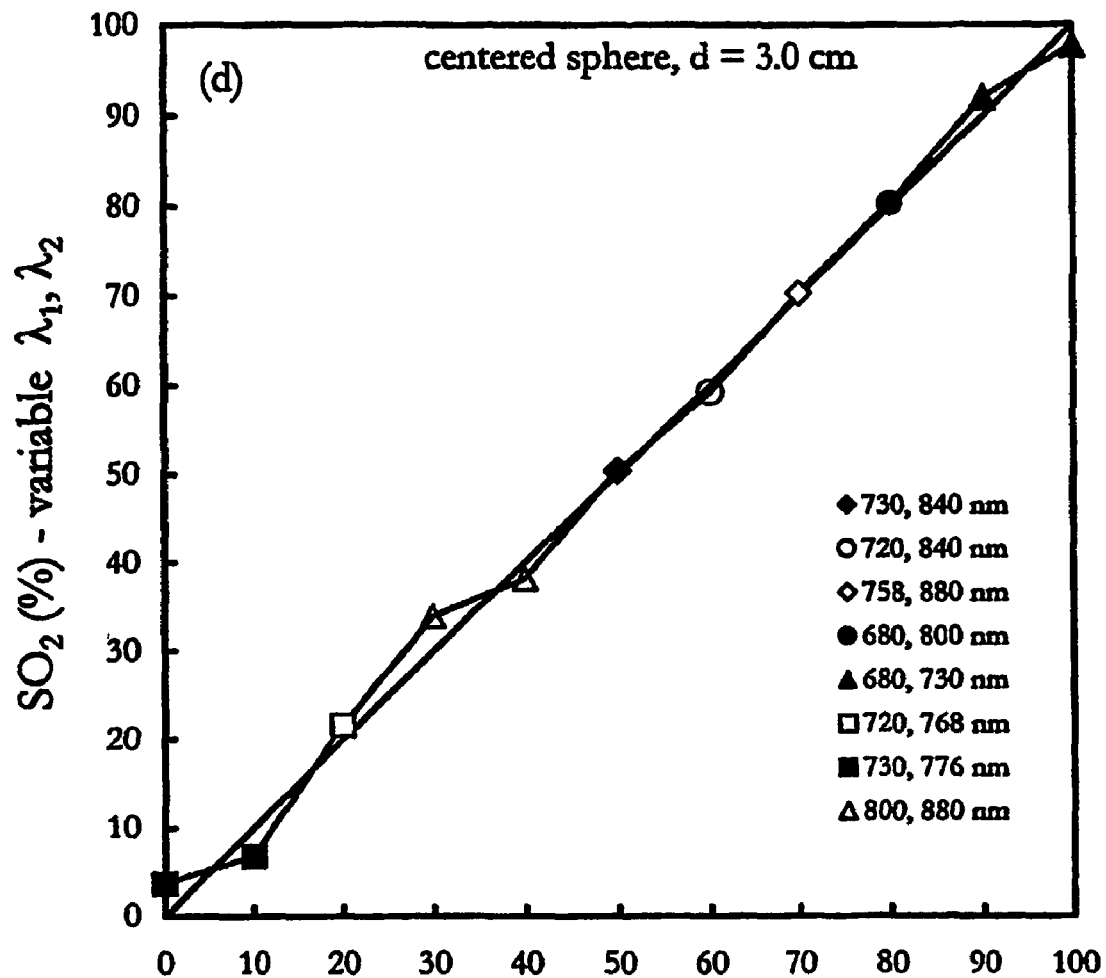
FIG. 21 is a graph obtained using the new methods for a selected wavelength pair for a 3.0 cm-diameter sphere (on the mid-line between source and detector) having a range of oxygenation levels.
Figure 22:
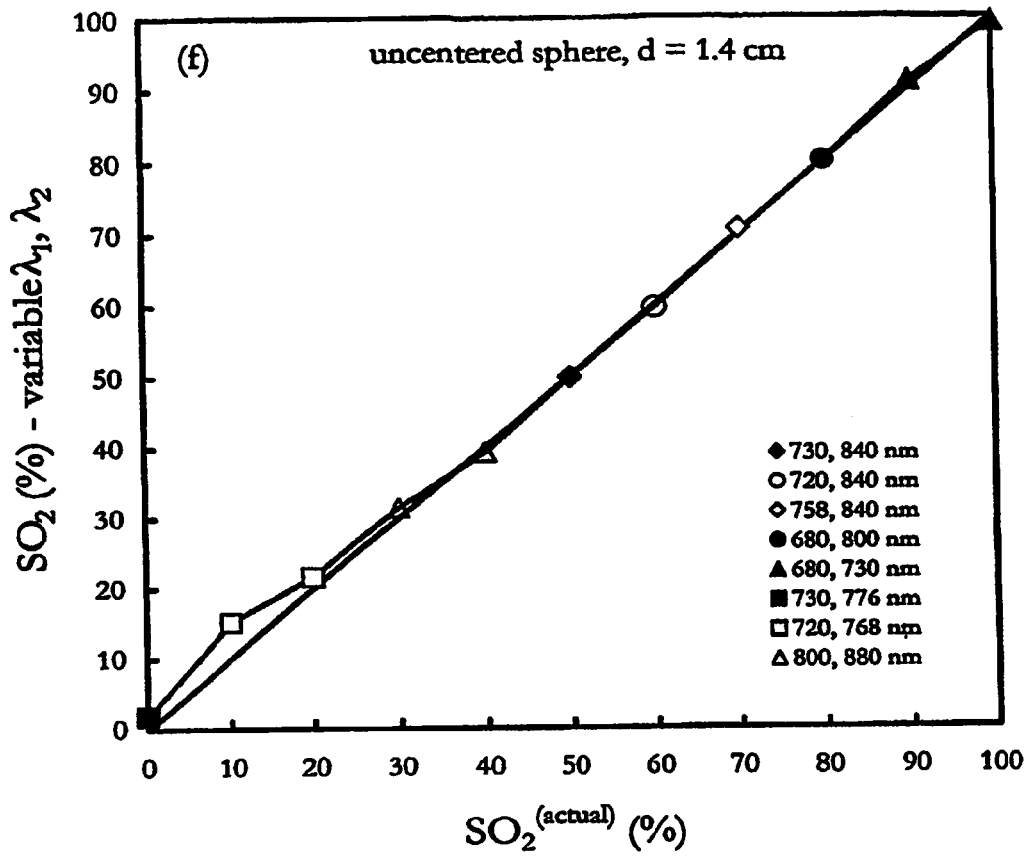
FIG. 22 is a graph obtained using the new methods for a selected wavelength pair for a 1.4 cm diameter sphere (off the mid-line by 1.5 cm) having a range of oxygenation levels.
Figure 23:
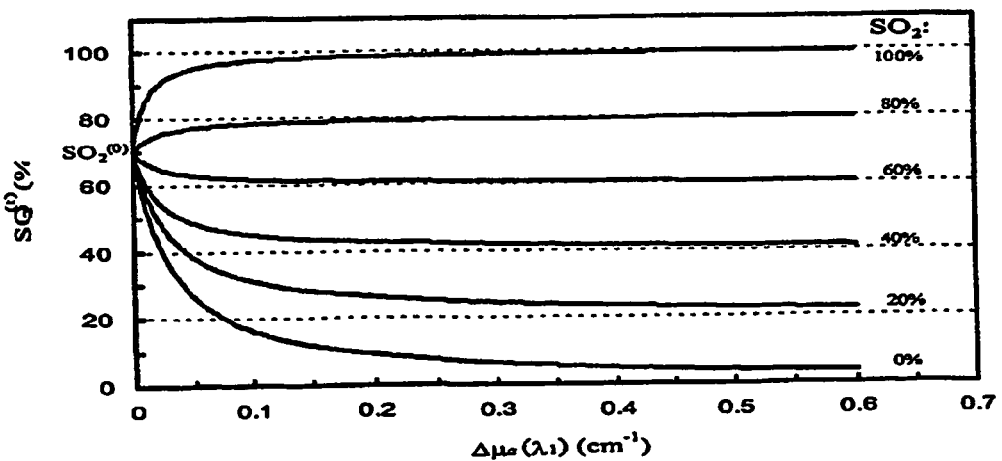
FIG. 23 is a graph of $SO_2^{(r)}$ versus $\Delta\mu_a(\lambda_1)$ for $SO_2$ values of 0, 20, 40, 60, 70, 80, and 100%.

The resulting spectra of the product $\mu_{s0}'\Delta\mu_a$ for $SO_2$ values of 0, 20, 40, 60, 80, and 100% are reported in FIG. 16. On the basis of Eq. (3), the spectra of FIG. 16 are representative of the spectra of $\Delta I/I_0|_{max}$. The hemoglobin saturation in the different lesions were compared: (1) by using Eq. (5) and a ratio $\Delta\mu_a(\lambda_2)/\Delta\mu_a(\lambda_1)$) computed with perturbation theory [Eq. (2)] from the intensity change $\Delta I/I_0|_{max}$ measured at two fixed wavelengths; and (2) by using the new methods [Eq. (7)] at two wavelengths that are at least 40 nm apart and that minimize the absolute value of the difference $\Delta I/I_0|_{max}(\lambda_2) - \Delta I/I_0|_{max}(\lambda_1)$ Both approaches take the background reduced scattering coefficient as input, which was known in our theoretical computations, and which can be measured with time-resolved methods in a practical implementation to the human breast. The results of the perturbation analysis for a number of wavelength pairs are shown in FIG. 17 for a 1.4 cm-diameter sphere (on the mid-line between source and detector), in FIG. 18 for a 3.0 cm-diameter sphere (on the mid-line between source and detector), and in FIG. 19 for a 1.4 cm diameter sphere off the mid-line by 1.5 cm. The results of the new methods are shown in FIG. 20 (sphere diameter: 1.4 cm; on the mid-line), FIG. 21 (sphere diameter: 3.0 cm; on the mid-line), and FIG. 22 (sphere diameter: 1.4 cm; 1.5 cm off the mid-line).

The improved fit obtained to the actual oxygenation levels using the new methods is evident by comparing FIGS. 22-24 to FIGS. 19-21. None of the lines obtained using prior art perturbation analysis for a pair of wavelengths achieved a comparable fit to lines obtained using the new methods with a selected pair of wavelengths. These results show that the new methods provided accurate measurements of the oxygenation of spherical regions over the full range of oxygenation values and independent of the size and location of the sphere. The wavelength pairs that minimize the difference between $\Delta I/I_0|_{max}^{(\lambda_1)}$ and $\Delta I/I_0|_{max}^{(\lambda_2)}$ (which is the criterion used to select the particular wavelength pairs in FIGS. 22, 23, and 24) for the cases of $SO_2$ equal to 0, 20, 40, 60, 80, and 100% are indicated in FIG. 16. In FIG. 16, the wavelengths used are shown by the dashed lines, and the symbols identify the wavelength pairs that minimize the difference between $\Delta I/I_0|_{max}^{(\lambda_1)}$ and $\Delta I/I_0|_{max}^{(\lambda_2)}$ for each value of $SO_2$.

Additional Computational Methods

The new techniques discussed above quantify the oxygen saturation associated with $\Delta\mu_a$, i.e., with the additional absorption at the tumor location with respect to the background tissue [see Eq. (5)]. These techniques are useful where (1) the absorption at the tumor location results from the sum of the background (healthy tissue) absorption ($\mu_{a0}$) plus the tumor contribution ($\mu_a^{(t)} \equiv \Delta\mu_a$), or if (2) the tumor absorption $\mu_a^{(t)}$ is equal to $\mu_{a0} + \Delta\mu_a$, and $\Delta\mu_a \gg \mu_{a0}$ (high-contrast tumor). In the case where $\lambda_a^{(t)} = \mu_{a0} + \Delta\mu_a$, but $\Delta\mu_a$ is not much greater than $\mu_{a0}$, the tumor saturation $SO_2^{(t)}$ is more appropriately given by:

$$SO_2^{(t)} = \frac{\varepsilon_{Hb}(\lambda_2) - \varepsilon_{Hb}(\lambda_1)\frac{\mu_{a0}(\lambda_2) + R\Delta\mu_a(\lambda_1)}{\mu_{a0}(\lambda_1) + \Delta\mu_a(\lambda_1)}}{[\varepsilon_{Hb}(\lambda_2) - \varepsilon_{HbO2}(\lambda_2)] + [\varepsilon_{HbO2}(\lambda_1) - \varepsilon_{Hb}(\lambda_1)]\frac{\mu_{a0}(\lambda_2) + R\Delta\mu_a(\lambda_1)}{\mu_{a0}(\lambda_1) + \Delta\mu_a(\lambda_1)}}, \quad (11)$$

where $R = \Delta\mu_a(\lambda_2)/\Delta\mu_a(\lambda_1)$. Because R is on the order of $\mu_{s0}'(\lambda_1)/\mu_{s0}(\lambda_2)$ it is typically close to 1. Consequently, $SO_2^{(t)}$ given by Eq. (11) tends to the background saturation ($SO_2^{(0)}$) in the limit $\Delta\mu_a \rightarrow 0$ and to the saturation based on $\Delta\mu_a$ ($SO_2$) in the limit $\Delta\mu_a \gg \mu_{a0}$. The derivative of $SO_2^{(t)}$ with respect to $\Delta\mu_a(\lambda_1)$ at constant R is given by:

$$\left(\frac{\partial SO_2^{(t)}}{\partial \Delta\mu_a^{(\lambda_1)}}\right)_R = \quad (12)$$

$$\frac{[\mu_{a0}(\lambda_2) + R\mu_{a0}(\lambda_1)][\varepsilon_{Hb}(\lambda_1) - \varepsilon_{HbO2}(\lambda_1) - \varepsilon_{Hb}(\lambda_1)\varepsilon_{HbO2}(\lambda_2)]}{\{[\varepsilon_{Hb}(\lambda_2) - \varepsilon_{HbO2}(\lambda_2)][\mu_{a0}(\lambda_1) + \Delta\mu_a(\lambda_1)] + [\varepsilon_{HbO2}(\lambda_1) - \varepsilon_{Hb}(\lambda_1)][\mu_{a0}(\lambda_2) + R\Delta\mu_a(\lambda_1)]\}^2}$$

Equation (12) shows that for any given value of R, the sign of the derivative of $SO_2^{(t)}$ with respect to $\Delta\mu_a(\lambda_1)$ is independent of $\Delta\mu_a(\lambda_1)$. As a result, $SO_2^{(t)}$ monotonically increases (or decreases) from $SO_2^{(0)}$ to $SO_2$ as the tumor contrast increases. This is graphically shown in FIG. 23 for the case $SO_2^{(0)} = 70\%$, $\mu_{a0}(800 \text{ nm}) = 0.02 \text{ cm}^{-1}$ (a reasonable estimate of the background hemoglobin absorption in breast tissue), and $SO_2$ values of 0, 20, 40, 60, 80, and 100%. Therefore, the sign of $SO_2^{(t)} - SO_2^{(0)}$, which indicates whether the tumor is more oxygenated or less oxygenated than the background healthy tissue, is accurately given by the sign of $SO_2 - SO_2^{(0)}$ independent of the tumor contrast. Furthermore, FIG. 23 indicates that for $\Delta\mu_a > 0.1 \text{ cm}^{-1}$ and tumor saturation values greater than 40%, $SO_2^{(t)}$ and $SO_2$ differ by no more than ~5%. Using an estimate of $\Delta\mu_a(\lambda_1)$, for instance on the basis of Eq. (2), can provide a refinement of the tumor saturation measurement from the values of $SO_2$ (obtained using the new methods) and $SO_2^{(0)}$ (measured on healthy breast tissue). This use of such an estimate is appropriate where the tumor absorption is better represented by $\mu_{a0} + \Delta\mu_a$ then by $\Delta\mu_a$.

In Vivo Results

Figures 1, 24A:
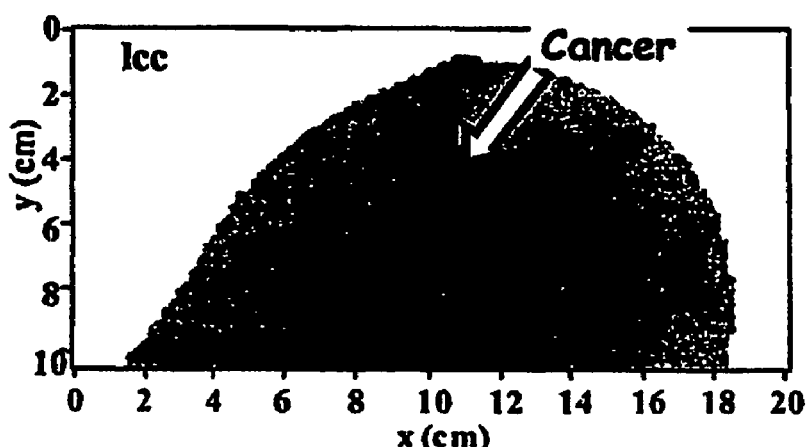
Figures 2, 24A:
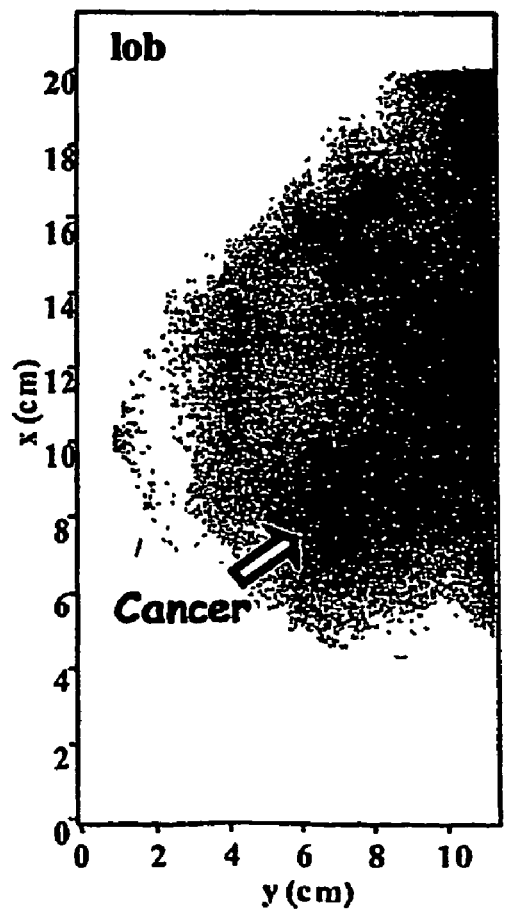
Figures 1, 24B:
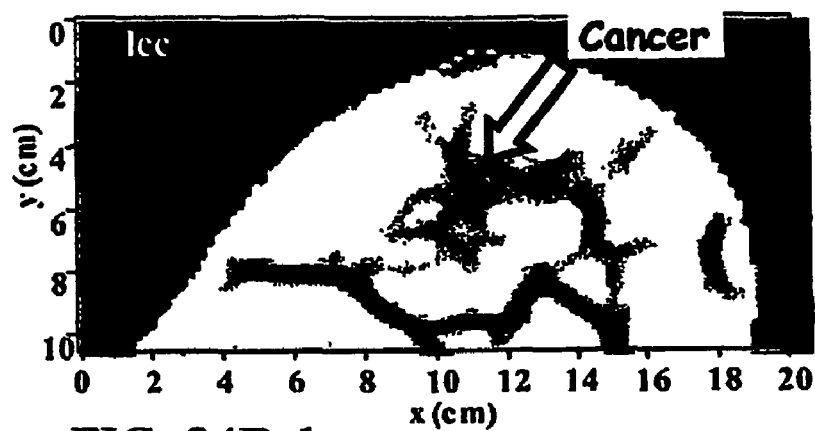
Figures 2, 24B:
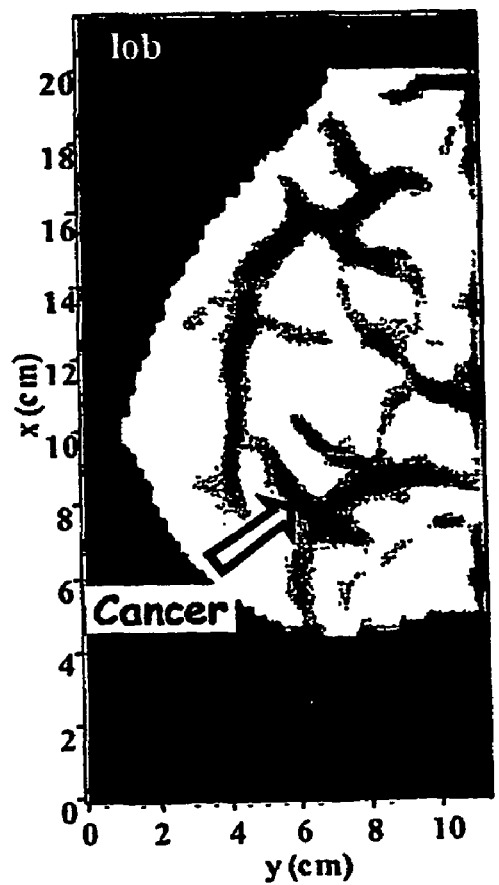
Figures 1, 24C:
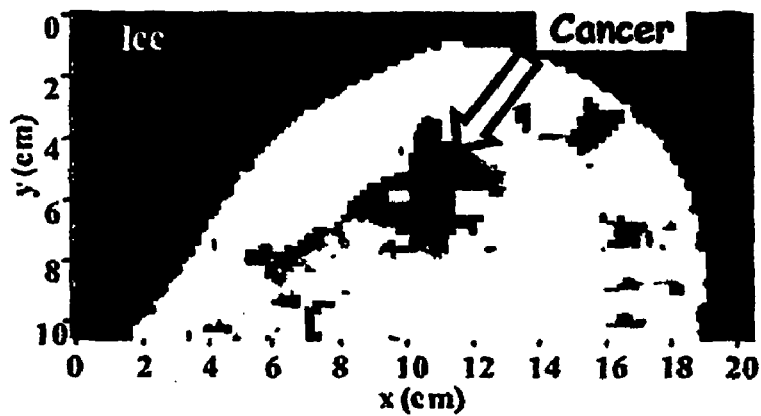
Figures 2, 24C:
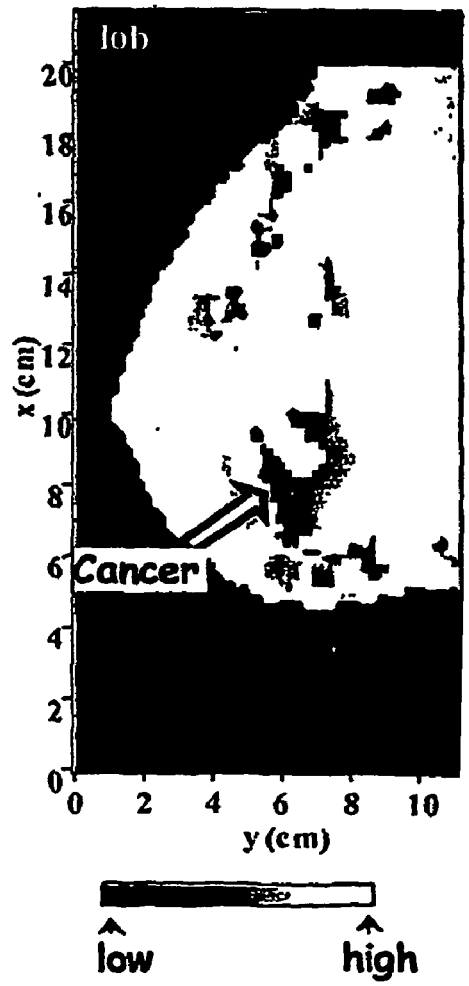

The techniques and methods discussed above have been applied to produce images of in vivo tumors in human tissue. For example, FIGS. 24*a*1 to 24*c*2 show left cranio-caudal (lcc) and left oblique views (lob) of a 3.0 cm invasive ductal carcinoma in the left breast of a 53-year-old patient. The location of the lesion is known from x-ray mammography, and the nature of the lesion is known from biopsy or physical examination. FIGS. 24*a*1 and *a*2 show intensity (N) images of light transmitted through the breast. FIGS. 24*b*1 and *b*2 show second-derivative (N") images of the transmitted image; and FIGS. 24*c*1 and *c*2 show the relative oxygenation index of the features.

The second derivative image is generated by processing the N-image through a low-pass-filter (smoothing), calculating the spatial second derivative of N at each pixel in four directions (horizontal, vertical, two diagonals), taking the minimum of the four directional second derivatives to enhance the detection of directional structures such as blood vessels, displaying on a gray scale the pixels associated with a negative second derivative (i.e., those corresponding to absorbance maxima), and setting the positive-second-derivative pixels to white.

The cancer is detected in the left craniocaudal (lcc) view of the intensity image (FIG. 24*a*1), together with a conspicuous blood vessel, but is not readily visible in the left oblique (lob) view (FIG. 24*a*2). The image contrast is enhanced in the second-derivative (N") images (FIGS. 24*b*1 and *b*2), which display negative second-derivative values (gray areas) at the cancer location in both lcc and lob views. However, additional inhomogeneities (most likely associated with blood vessels) appear in the second-derivative images (24*b*1 and *b*2) that were not visible in the intensity images (FIG. 24*a*1 and *a*2). The increased sensitivity afforded by the second-derivative images may be effectively complemented by the functional information provided by the oxygenation index images. In this case, the tumor location corresponds to areas of lowest oxygenation index in both the lcc and lob views (see FIGS. 24c1 and c2).

Figure 25C:

FIGS. 25a to 25c show left cranio-caudal (lcc) views of a 1.5 benign mastopathy in the left breast of a 62-year-old patient. FIG. 25a shows an intensity (N) image of light transmitted through the breast. FIG. 25b shows a second-derivative (N") image of the transmitted image; and FIG. 25c shows the relative oxygenation index of the features. The mastopathy is visible in both the intensity image (FIG. 25a) and the second-derivative image (FIG. 25b). However, oxygenation level of the mastopathy is relatively high, as shown in the oxygenation level image (FIG. 25c), indicating that the tumor is benign.

Figures 26A, 26B, 26C:
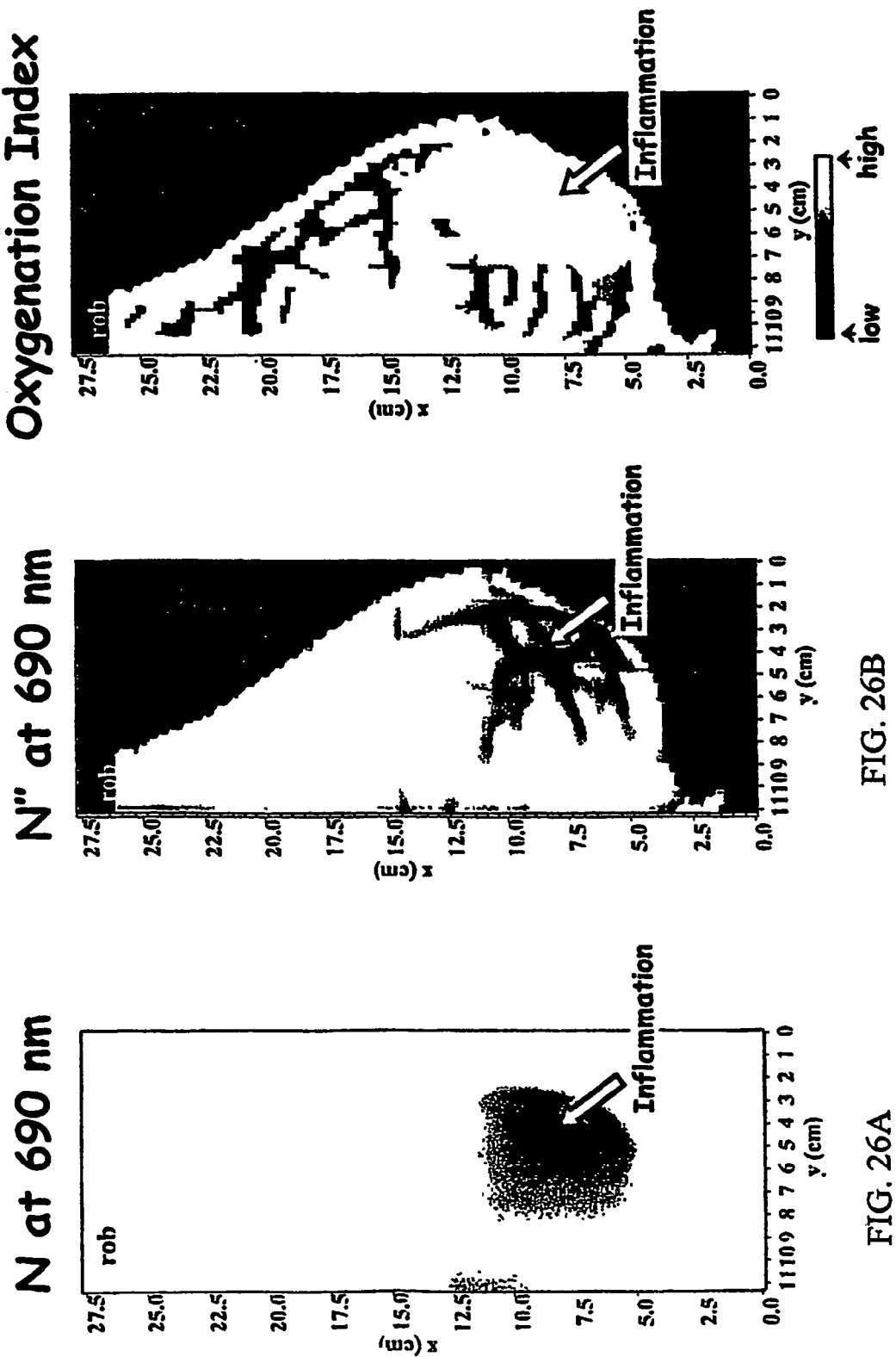
FIGS. 26a to 26c are a series of images of benign inflammation in a breast.

FIGS. 26a to 26c show a right oblique (rob) view of benign inflammation in a breast of a 65-year-old patient. FIG. 26a shows an intensity (N) image of light transmitted through the breast. FIG. 26b shows a second-derivative (N") image of the transmitted image; and FIG. 26c shows the relative oxygenation index of the features. The inflammation shows up as the dominant feature in the N-image as well as in the N"-image, but structural information is much more defined in the N"-image. Furthermore, the oxygenation index image shows the highest value of oxygenation in the region of the inflammation, and lower oxygenation values elsewhere, indicating that the inflammation is benign.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims. For example, the new techniques can be used to image brain tissue and assess brain activity by measuring absolute levels of oxygenation, or to image muscle tissue and identify ischemic or underperfused tissue regions.

What is claimed is:

1. A method of determining whether a tumor in a tissue sample is malignant or benign, the method comprising:
   (a) selecting two wavelengths of light to minimize a difference between relative changes in intensity of light transmitted through the tumor for the two wavelengths, wherein the relative changes in intensity of the light for each wavelength are measured relative to a background intensity of light transmitted through the sample;
   (b) obtaining measures of background reduced scattering coefficients of the sample at the two wavelengths;
   (c) calculating an absolute oxygenation level of the tumor in the sample by using the relative changes in intensity of the light for the two wavelengths and the measures of the background reduced scattering coefficients of the sample for the two wavelengths; and
   (d) determining whether the tumor is malignant or benign based on the value of the calculated absolute oxygenation level.

2. The method of claim 1, wherein the tissue sample is selected from the group consisting of breast tissue, brain tissue, and muscle tissue.

3. The method of claim 1, wherein the two wavelengths of light are in the near infrared spectrum.

4. The method of claim 1, wherein the difference between the relative changes in intensity is zero.

5. The method of claim 1, wherein the absolute oxygenation level of the tumor is calculated using a formula $$SO_2 = \frac{\varepsilon_{Hb}(\lambda_2) - \varepsilon_{Hb}(\lambda_1)\frac{\mu'_{s0}(\lambda_1)\Delta I/I_0\,|_{max}^{(\lambda_2)}}{\mu'_{s0}(\lambda_2)\Delta I/I\,|_{max}^{(\lambda_1)}}}{[\varepsilon_{Hb}(\lambda_2) - \varepsilon_{HbO2}(\lambda_2)] + [\varepsilon_{HbO2}(\lambda_1) - \varepsilon_{Hb}(\lambda_1)]\frac{\mu'_{s0}(\lambda_1)\Delta I/I_0\,|_{max}^{(\lambda_2)}}{\mu'_{s0}(\lambda_2)\Delta I/I\,|_{max}^{(\lambda_1)}}},$$

wherein:
   $SO_2$ is the oxygenation level of the region;
   $\Delta I/I_0|_{max}^{(\lambda_1)}$ is a maximum value of a relative change in intensity at a first wavelength in the pair of wavelengths;
   $\Delta I/I_0|_{max}^{(\lambda_2)}$ is a maximum value of a relative change in intensity at a second wavelength in the pair of wavelengths;

$$\frac{\mu'_{s0}(\lambda_1)}{\mu'_{s0}(\lambda_2)}$$

is a ratio of the background reduced scattering coefficient at the first wavelength to the background reduced scattering coefficient at the second wavelength;
   $\epsilon_{Hb}(\lambda_1)$ and $\epsilon_{Hb}(\lambda_2)$ are molar extinction coefficients for deoxy-hemoglobin at the first and second wavelengths; and
   $\epsilon_{HbO2}(\lambda_1)$ and $\epsilon_{HbO2}(\lambda_2)$ are molar extinction coefficients for oxy-hemoglobin at the first and second wavelengths.

6. The method of claim 1, further comprising, prior to selecting the two wavelengths of light:
   (e) illuminating the sample with a plurality of wavelengths of light; and
   (f) detecting light transmitted through the sample at a plurality of locations,
   wherein the two wavelengths of light are selected from among wavelengths of the light transmitted through the sample.

7. The method of claim 6, further comprising (g) displaying an image of the absolute oxygenation level at the plurality of locations within the tissue sample.

8. The method of claim 1, further comprising (e) storing values of the absolute oxygenation level of the tumor in a computer-readable medium.

9. A method of determining whether a tumor in a tissue sample is malignant or benign, the method comprising:
   (a) obtaining thicknesses of the sample and intensities of light transmitted through the sample at a plurality of locations for two wavelengths of light;
   (b) calculating spatial second derivatives of products of the sample thicknesses and the intensities of the transmitted light at the locations for the two wavelengths of light;
   (c) calculating an oxygenation level of the tumor based on the spatial second derivatives for the two wavelengths of light, the molar extinction coefficients of oxy-hemoglobin for the two the wavelengths of light, the molar extinction coefficients of hemoglobin for the two wavelengths of light, relative changes in intensity of the light for the two wavelengths of light and the measures of the background reduced scattering coefficients of the sample for the two wavelengths of light;

(d) calculating an oxygenation level of non-tumor regions of the tissue sample based on the spatial second derivatives for the two wavelengths of light, the molar extinction coefficients of oxy-hemoglobin for the two wavelengths of light, the molar extinction coefficients of hemoglobin for the two wavelengths of light, relative changes in intensity of the light for the two wavelengths of light, and the measures of the background reduced scattering coefficients of the sample for the two wavelengths of light; and (e) comparing the oxygenation level of the tumor with the oxygenation level of non-tumor regions of the sample to determine whether the tumor is malignant or benign.

10. The method of claim 9, wherein the tissue sample is selected from the group consisting of breast tissue, brain tissue, and muscle tissue.

11. The method of claim 9, wherein the two wavelengths of light are in the near infrared spectrum.

12. The method of claim 9, wherein the oxygenation level of a region of the sample is calculated using a formula $$OL = \frac{\Delta[HbO_2]^*}{\Delta[HbO_2]^* + \Delta[Hb]^*},$$

wherein $$\Delta[HbO_2]^* = \frac{\left(\sum_i N''(\lambda_i)\varepsilon_{HbO2}(\lambda_i)\right)\left(\sum_i \varepsilon_{Hb}^2(\lambda_i)\right) - \left(\sum_i N''(\lambda_i)\varepsilon_{Hb}(\lambda_i)\right)\left(\sum_i \varepsilon_{HbO2}(\lambda_i)\varepsilon_{Hb}(\lambda_i)\right)}{\left(\sum_i \varepsilon_{HbO2}^2(\lambda_i)\right)\left(\sum_i \varepsilon_{Hb}^2(\lambda_i)\right) - \left(\sum_i \varepsilon_{HbO2}(\lambda_i)\varepsilon_{Hb}(\lambda_i)\right)^2},$$

$$\Delta[Hb]^* = \frac{\left(\sum_i N''(\lambda_i)\varepsilon_{Hb}(\lambda_i)\right)\left(\sum_i \varepsilon_{HbO2}^2(\lambda_i)\right) - \left(\sum_i N''(\lambda_i)\varepsilon_{HbO2}(\lambda_i)\right)\left(\sum_i \varepsilon_{HbO2}(\lambda_i)\varepsilon_{Hb}(\lambda_i)\right)}{\left(\sum_i \varepsilon_{HbO2}^2(\lambda_i)\right)\left(\sum_i \varepsilon_{Hb}^2(\lambda_i)\right) - \left(\sum_i \varepsilon_{HbO2}(\lambda_i)\varepsilon_{Hb}(\lambda_i)\right)^2},$$

and wherein:
- OL is the oxygenation level of the tumor;
- i is a wavelength index for the two wavelengths;
- $\varepsilon_{HbO2}$ and $\varepsilon_{Hb}$ are the molar extinction coefficients of oxy-hemoglobin and deoxy-hemoglobin, respectively;
- $\Delta[HbO_2]^*$ and $\Delta[Hb]^*$ are relative values for the spatial changes in the concentrations of oxy-hemoglobin and deoxy-hemoglobin, respectively; and
- N'' is a spatial second derivative of an intensity of transmitted light.

13. The method of claim 9, further comprising, prior to obtaining the intensities of the transmitted light for two wavelengths:

(f) illuminating the sample with a plurality of wavelengths of light; and (g) detecting light transmitted through the sample at a plurality of locations, wherein the two wavelengths of light are selected from among wavelengths of the light transmitted through the sample.

14. The method of claim 9, further comprising (f) displaying an image of oxygenation levels at the plurality of locations within the tissue sample.

15. The method of claim 9, further comprising (f) storing values of oxygenation levels at a plurality of locations within the tissue sample in a computer-readable medium.

* * * * *

UNITED STATES PATENT AND TRADEMARK OFFICE
CERTIFICATE OF CORRECTION

| | | |
|---|---|---|
| PATENT NO. | : 7,962,187 B2 | |
| APPLICATION NO. | : 10/507336 | |
| DATED | : June 14, 2011 | |
| INVENTOR(S) | : Sergio Fantini | |

It is certified that error appears in the above-identified patent and that said Letters Patent is hereby corrected as shown below:

Column 20:

In Claim 5, at line 5, delete "region" and insert -- tumor --, therefor;

In Claim 5, at line 6, before "relative," delete "a" and insert -- the --, therefor;

In Claim 5, at line 8, before "relative," delete "a" and insert -- the --, therefor;

In Claim 9, at line 12, before "wavelengths," delete "the".

Signed and Sealed this
Seventeenth Day of July, 2012

David J. Kappos
*Director of the United States Patent and Trademark Office*